United States Patent
Harju et al.

(10) Patent No.: US 6,891,618 B2
(45) Date of Patent: *May 10, 2005

(54) OPTICAL INSTRUMENT AND PROCESS FOR MEASUREMENT OF SAMPLES

(75) Inventors: Raimo Harju, Turku (FI); Christer Isaksson, Turku (FI)

(73) Assignee: Wallac Oy, Tûrku (FI)

( * ) Notice: Subject to any disclaimer, the term of this patent is extended or adjusted under 35 U.S.C. 154(b) by 12 days.

This patent is subject to a terminal disclaimer.

(21) Appl. No.: 09/947,571

(22) Filed: Sep. 7, 2001

(65) Prior Publication Data

US 2003/0048447 A1 Mar. 13, 2003

(51) Int. Cl.[7] .............................................. G01N 21/25
(52) U.S. Cl. ........................ 356/417; 356/418; 356/344
(58) Field of Search ................................ 356/417, 418, 356/419, 426, 427, 213, 344

(56) References Cited

U.S. PATENT DOCUMENTS

| | | | |
|---|---|---|---|
| 4,589,776 A | * 5/1986 | Carver et al. | 356/367 |
| 5,780,857 A | * 7/1998 | Harju et al. | 250/458.1 |
| 5,825,478 A | * 10/1998 | Wilcox et al. | 356/73 |
| 5,973,330 A | 10/1999 | Hayashi | |
| 6,042,785 A | * 3/2000 | Harju | 422/52 |
| 6,097,025 A | 8/2000 | Modlin et al. | |
| 6,200,818 B1 | 3/2001 | Eigen et al. | |

FOREIGN PATENT DOCUMENTS

| | | |
|---|---|---|
| DE | 199 19 091 A1 | 11/2000 |
| EP | 0 896 237 A1 | 2/1999 |
| WO | 98/54077 | 12/1998 |
| WO | 01/04608 A1 | 1/2001 |

* cited by examiner

*Primary Examiner*—Gregory J. Toatley, Jr.
*Assistant Examiner*—Roy M. Punnoose
(74) *Attorney, Agent, or Firm*—Young & Thompson

(57) ABSTRACT

The present invention relates generally to the field of biochemical laboratory. More particularly the invention relates to the improved and more accurate instrumental features of equipment used as e.g. fluorometers, photometers and luminometers. The object of the invention is achieved by providing an optical measurement instrument where there is an interface (218, 223, 233a, 233b, 238) for a changeable optical module (240), and excitation and/or emission beam is guided through an aperture of the optical module. This allows performing various types of measurements by changing an optical module without a problem lenses becoming unclean due to manual handling of the optical modules. The invention also makes possible to achieve an accurate measurement location and area within a sample.

47 Claims, 14 Drawing Sheets

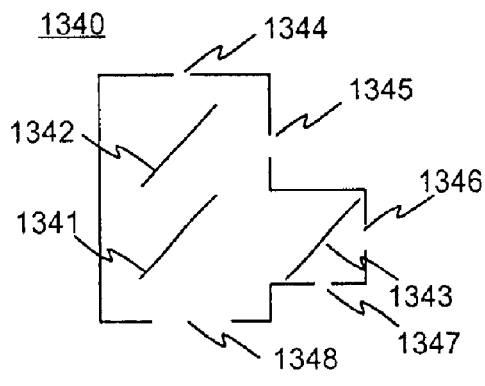
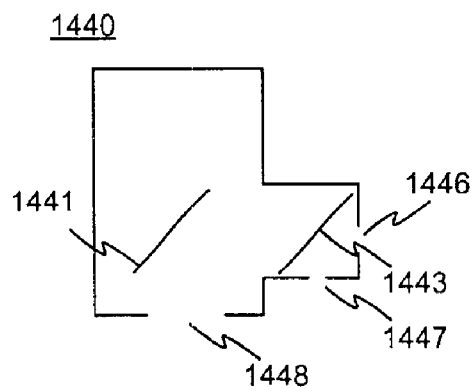
FIG. 13  FIG. 14
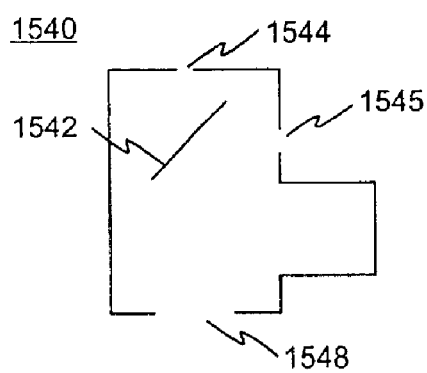
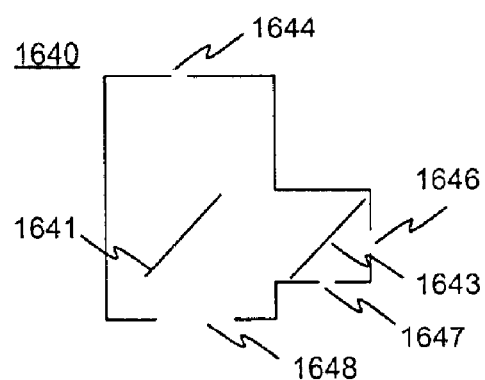
FIG. 15  FIG. 16
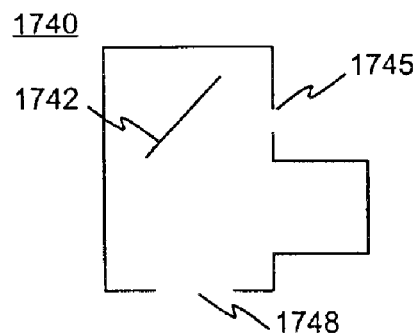
FIG. 17

OPTICAL INSTRUMENT AND PROCESS FOR MEASUREMENT OF SAMPLES

BACKGROUND OF THE INVENTION

The present invention relates generally to the field of biochemical laboratory instrumentation for different applications of measuring properties of samples on e.g. microtitration plates and corresponding sample supports. More particularly the invention relates to the improved, reliable and more accurate instrumental features of equipment used as e.g. fluorometers, photometers and luminometers.

The routine work and also the research work in analytical biochemical laboratories and in clinical laboratories are often based on different tags or labels coupled on macromolecules under inspection. The typical labels used are different radioactive isotopes, enzymes, different fluorescent molecules and e.g. fluorescent chelates of rare earth metals.

The detection of enzyme labels can be performed by utilizing its natural biochemical function, i.e. to alter the physical properties of molecules. In enzyme immunoassays colourless substances are catalysed by enzyme to colourful substances or non-fluorescent substances to fluorescent substances.

The colourful substances are measured with absorption, i.e. photometric measurement. In the photometric measurement the intensity of filtered and stabilized beam is first measured without any sample and then the sample inside one plate is measured. The absorbance i.e. the absorption values are then calculated.

The fluorescent measurement is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies.

A further measurement method is chemiluminescence measurement where emission of a substance is measured from a sample without excitation by illumination. Thus any photoluminometer can also be used as a chemiluminometer.

The typical instruments in analytical chemical research laboratories are the different spectroscopic instruments. Many of them are utilizing optical region of electromagnetic spectrum. The two common types of instruments are the spectrophotometers and the spectrofluorometers. These instruments comprise usually one or two wavelength dispersion devices, like monochromators. The dispersion devices make them capable to perform photometric and luminescence measurements throughout the optical spectrum.

FIG. 1 illustrates an advanced prior art optical analyser, especially the optical components and the different optical paths. The instrument has two illumination sources, a continuous wave lamp (cw-lamp) 112a and a pulse lamp 112b. The cw-lamp can be used for continuous wave photoluminescence excitation and for absorption measurements.

Infrared part of radiation from the cw-lamp 112a is absorbed by a filter 104, and after transiting a stray-light aperture plate 105, the optical radiation is collimated with a lens 115a through an interference filter 114a located in a filter wheel 114.

The light beam is focused with a lens 113a, similar to the lens 114a, into a light guide 118, which isolates the measuring head thermally and mechanically. It also shields the measuring unit for the stray light from the cw-lamp. The optical radiation from an output aperture plate 106 of a light guide 118 is collimated with a lens 107, similar to the lens 115a. The radiation beam is reflected by a beam-splitter mirror 141 inside a mirror block 140, and passed through a sample well 181 and through an entrance window 122 of a photometric detector unit 132.

The mirror block 140 is located on the upper side of the sample. Its function is to reflect the horizontal light beam from the selected lamp downwards to the sample and to reflect a portion of this beam by a mirror 143 into a reference photodiode 119, and also to allow the emission from the sample to travel upwards to the detector 132.

The emission unit comprises optical components, which are lenses 133, 135, a filter 134a in filter slide 134, a combined shutter and aperture slide 136 and a detector 132, such as a photo-multiplier. The detector 132 is used in the fast photon counting mode where the pulses from photo-multiplier anode are first amplified and then fed through a fast comparator 191 and gate 192 counter 193. The comparator rejects the pulses, which are lower than the pre-adjusted reference level. The fast counting electronics is equipped with a gate in the front of the counter. This gate is used in overall timings of the measurements.

The pulse-lamp unit is used in time-resolved photoluminescence measurement for long-living luminescence emission. It comprises a second lamp 112b, lenses 115b, 113b, and optical filters 114b in a filter slide for wavelength isolation. When this second lamp is used the mirror 141 must be rotated by 90 degrees in order to reflect the radiation to the sample. This can be achieved by using different optical modules for the two lamps.

There are certain limitations related to the prior art technology. When different optical modules are used for different measurements the optical module is usually changed when the measurement mode is changed. As the optical modules are manually handled the lenses of the optical module easily become unclean. This causes attenuation of the optical beams and thus may make the measurement results less accurate and less reliable. Another limitation of the prior art solutions relates to comparability of different measurements. When different optical modules are used for different measurements the optical path may be different and cause that the location or size of the measurement area in the sample may be vary for different types of measurements.

SUMMARY OF THE INVENTION

The object of the present invention is to provide an optical instrument for laboratory measurements, wherein the described disadvantages of the prior art are avoided or reduced. The object of the invention is therefore to achieve a measurement instrument with improved accuracy, reliability, comparability and/or efficiency for performing measurements from samples.

The object of the invention is achieved by providing an optical measurement instrument where there is an interface for a changeable optical module, and the interface is optically adapted to at least one aperture of the optical module for receiving or outputting an optical beam. The object is also achieved by a changeable optical module for a measurement instrument, the module comprising at least one aperture for receiving or outputting an optical beam. The optical module preferably comprises a dichroic mirror for separating the optical paths of emission and excitation beam, and possibly a second dichroic mirror for dividing an emission beam into two emission beams. The invention allows performing various types of measurements by changing an optical module without a risk of touching optical surfaces such as lenses. The invention also allows an accurate determination of the sample area to be measured.

An optical measurement instrument according to the invention for measuring samples, comprising a possible illumination source for forming an excitation beam, a detector for detecting an emission beam, an interface for a changeable optical module with a purpose of directing the excitation beam received from the illumination source into the sample and/or directing an emission beam received from the sample to the first detector, is characterized in that the interface further comprises means for adapting to at least one of said beams being transmitted through an aperture located on a wall of an optical module.

The invention also applies to a changeable optical module for an optical measurement instrument, the module comprising
means for receiving an excitation beam from an illumination source and means for directing the excitation beam to a sample, and/or
means for receiving an emission beam from the sample and means for outputting the emission beam received from the sample to a detector,
which is characterized in that the means for receiving and/or the means for outputting comprise(s) an aperture on an outer wall of the optical module module.

The invention also applies to a process for measurement of samples with an optical measurement instrument comprising at least one measurement head, possible means for providing excitation of a sample and means for measuring an emission from the sample, the process comprising the phases of
selecting a measurement mode,
selecting at least one changeable optical module for a measurement head, the optical module guiding the excitation beam from an illumination source into the sample and/or guiding at least one emission beam from a sample into at least one detector,
performing the selected optical measurement,
which is characterized in that in the step of selecting the optical module, a kind of optical module is selected, which has a separate aperture for receiving an excitation beam and/or for outputting an emission beam.

A method according to the invention for optical measurement of samples comprising the step of transmitting excitation/emission beam between the sample and a measurement head of an optical instrument, comprising transmitting said beam through an optical module of the measurement head, is characterized in that said beam is guided through an aperture located on an outer wall of the optical module.

Some preferred embodiments are described in the dependent claims.

An important advantage of the invention relates to achieving high measurement accuracy. The aperture(s) of the optical module preferably determine the measurement area within the sample. Therefore the measurement area can be separately determined for each optical module. And especially in the two-emission measurement it is possible to determine the measurement areas separately by dimensioning the respective apertures of the optical module for the two simultaneous or successive emissions.

The changeable optical modules with aperture(s) according to the invention thus allow the dimensioning of the aperture according to a specific measurement. This gives the ability to offer optional functions in measurement equipment. Equipment with a measurement head for one emission measurement can be easily upgraded into equipment, which has a measurement head for one emission or two emission measurements. For the upgrade it is only necessary to provide the equipment with an optical module, which includes a mirror for the second emission, and providing the equipment with the second detector, if not readily available in the equipment. The basic version of the equipment preferably includes the required optics for guiding the second emission beam from the optical module to the second detector. So new features can be upgraded without a need to make on-site optical calibrations for each upgraded feature.

The invention also allows the use of direct optical coupling in emission detection; attenuation caused by optical fibres can thus be avoided. Attenuation is also minimized by the fact that the number of lenses within the emission path is minimal due to the use of apertures according to the invention.

BRIEF DESCRIPTION OF THE DRAWINGS

These and other advantages of the invention will become apparent from the following detailed description and by referring to the drawings where:

FIG. 13 illustrates a first exemplary top head optical module for implementing the invention, FIG. 14 illustrates a second exemplary top head optical module for implementing the invention, FIG. 15 illustrates a third exemplary top head optical module for implementing the invention, FIG. 16 illustrates a fourth exemplary top head optical module for implementing the invention, FIG. 17 illustrates a fifth exemplary top head optical module for implementing the invention.

DETAILED DESCRIPTION OF THE INVENTION

Figure 1:
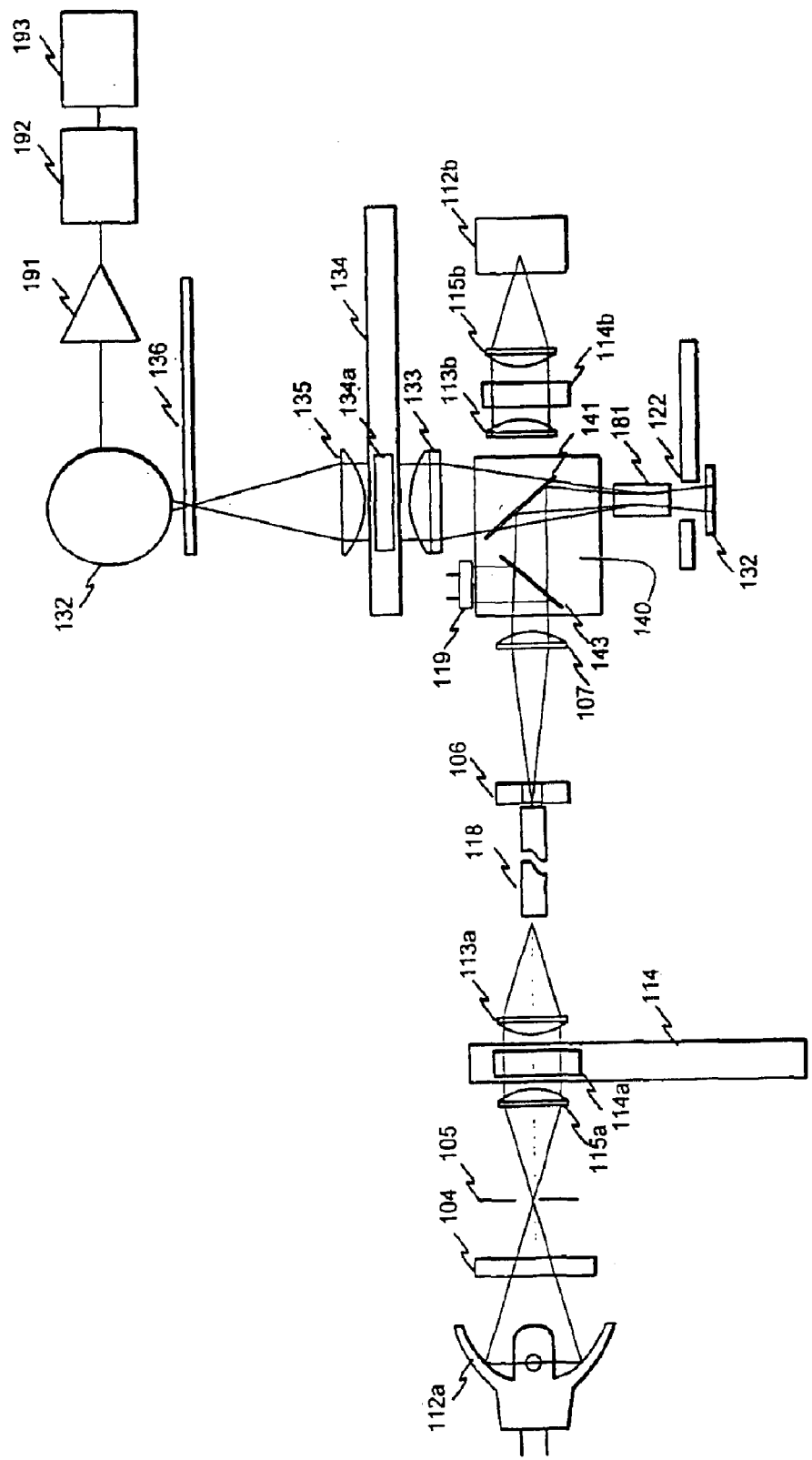
FIG. 1 is a schematic block diagram of a prior art optical unit of a measurement instrument.

FIG. 1 was already explained in the description of the prior art. In the following, the principle of the invention is first described referring to FIG. 2. Then, an example of a more detailed implementation is described referring to FIG. 3, which is a block diagram of exemplary analyser equipment according to the invention. Next there are some exemplary embodiments described for using an analyser according to the invention for double emission measurements, referring to FIGS. 4–12. After this, relating to FIGS. 13–22 there is a description of exemplary optical cubes comprising aperture(s) according to the invention and which can be used e.g. for the measurements referred to in FIGS. 4–12. Finally, examples of a process and a method for performing a measurement according to invention are described referring to flow diagrams in FIGS. 23 and 24.

Figure 2:
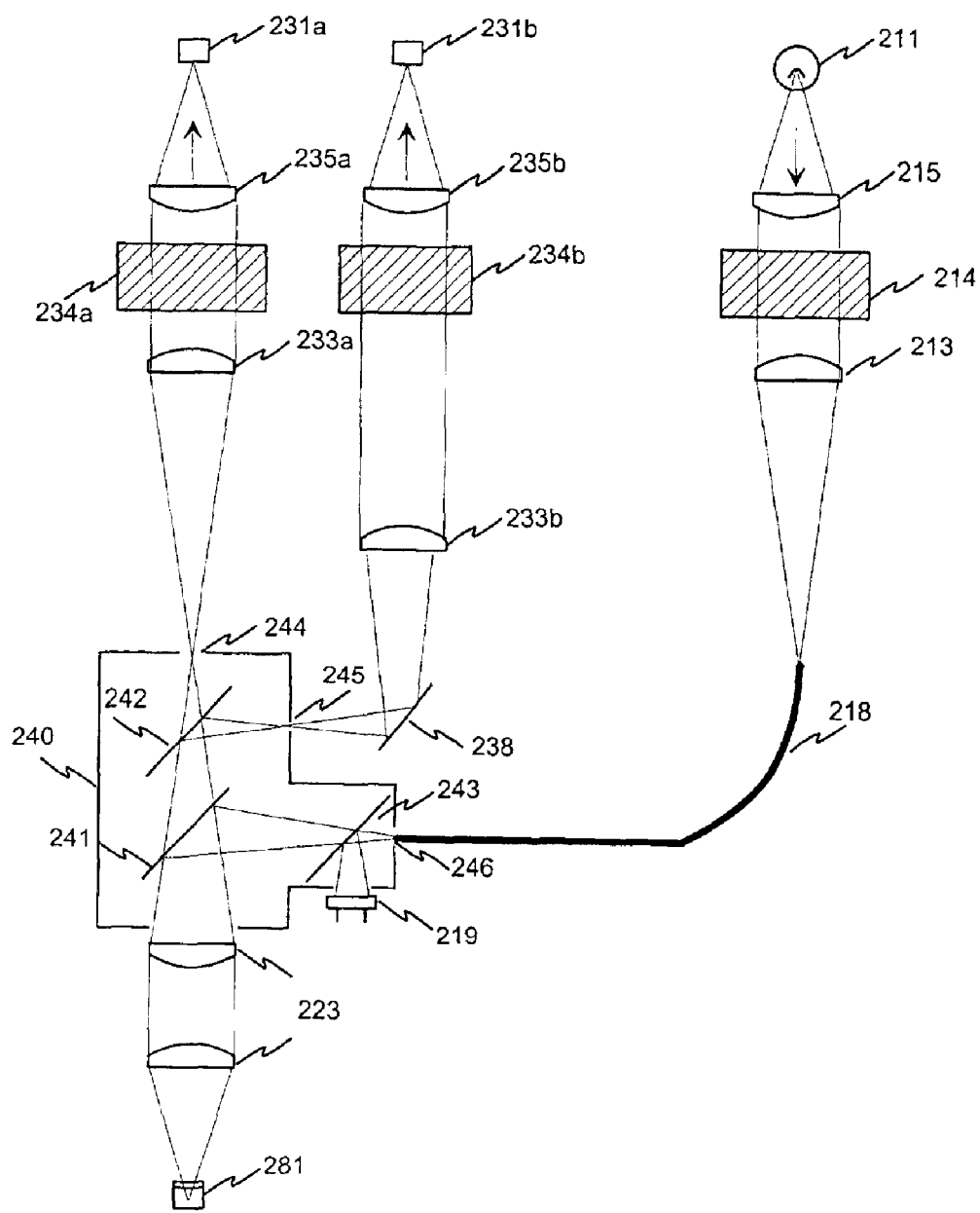
FIG. 2 is a schematic illustration of optical paths and main components of an exemplary optical unit for a measurement instrument according to the invention.

FIG. 2 illustrates main components and optical paths of an exemplary optical analyser instrument according to the invention. The instrument comprises an illumination source 211 for the excitation of a sample. The radiation from the lamp 211 is collimated with lens 215 and directed through an interference filter 214. Different filters can be selected for different wavelengths. The excitation beam is then focused to an end of a fibre optic guide 218, which guides it to an aperture 246 of an optical module according to the invention. The fibre optic guide is preferably a bundle of fibres, such as 200 pieces of fibres with a diameter of 100 $\mu$m. One important purpose of the fibre optic guide is to mix the light of the illumination source in order to avoid an uneven distribution of excitation beam within the sample volume to be measured. The excitation beam is guided through an aperture 246 of the optical module 240. The excitation beam is further directed into the sample 281 through an aperture of the optical module and a lens system 223. A part of the illumination light is reflected by a beam splitter mirror 243 and guided through an aperture into a reference detector 219 in order to give reference information on the actual illumination intensity. While the reference mirror is located in the changeable mirror block, the excitation filter differences can be compensated by modifying the properties of the reference mirror. This way high feedback accuracy is achieved. A beam splitter mirror can be produced e.g. by forming reflective coating for the mirror to be e.g. stripes or dots, which cover only a part of the mirror surface.

The emission beam from the sample 281 is directed with the lens system 223 through an aperture into the optical module 240, where it passes the (preferably) dichroic mirror 241. The dichroic mirror is preferably designed for each label so that it reflects excitation wavelength but transmits emission wavelengths. The emission beam is then divided inside the optical cube into two beams by a second mirror 242. The mirror is preferably a dichroic mirror, which functions as a filter so that a beam with a wavelength of the first emission is transmitted through the mirror and focused through an aperture 244 according to the invention to the first detector 231a. The beam with a wavelength of the second emission is reflected and guided focused through another aperture 245 to the second detector 231b. The second dichroic mirror is therefore also preferably designed for each label/pair of labels so that it transmits first emission wavelengths but reflects second emission wavelengths.

The first emission beam received from the aperture of the optical module is collimated with a lens 233a and directed through an interference filter 234a in order to prevent light with a wavelength outside the first emission from passing to the first detector. The first emission beam is then focused with lens 235a to the first detector 231a. The second emission beam received from another aperture of the optical module is reflected with a mirror 238 to a lens 233b where the beam is collimated and directed through a second interference filter 234b in order to prevent light with a wavelength outside the second emission from passing to the second detector. The second emission beam is then focused with lens 235a to the first detector 231a. The signals received from the detectors are then amplified and processed to achieve a value for the intensities of the first and second emissions. The excitation and emission parts of the instrument can be used, except for photoluminescence measurements, also to e.g. photometric and chemiluminescence measurements.

As already mentioned, an essential feature of the invention is that the excitation beam as well as two emission beams are adapted to be interfaced with a single changeable optical module, which preferably comprises apertures for each of the beams. This allows performing various types of measurements by changing just one optical module, and each of the measurements can be optimally performed with the specific optical module. The advantages of the invention become more apparent in the following more complete example of an optical instrument according to the invention.

Figure 3:
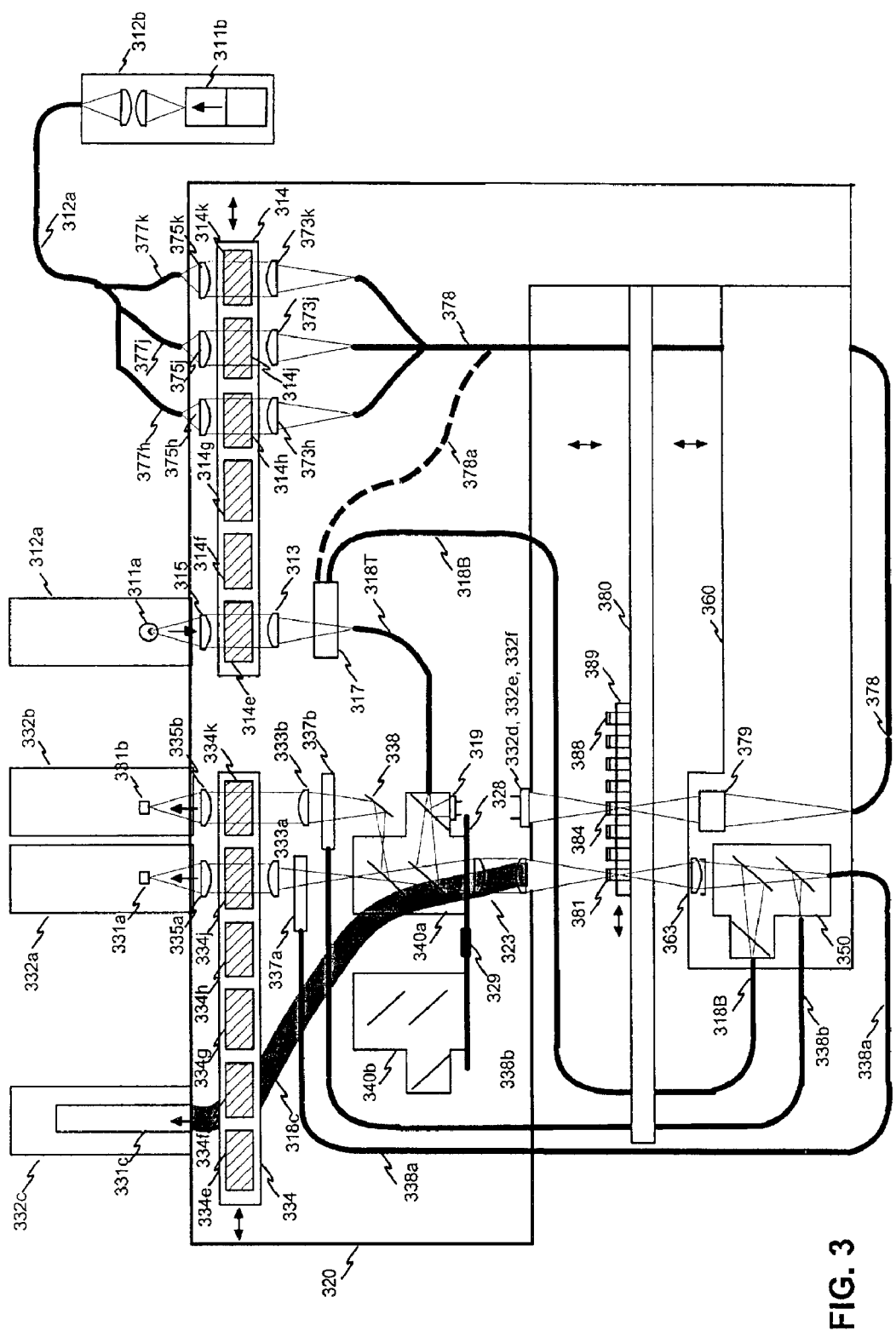
FIG. 3 is a schematic block diagram of an exemplary measurement instrument according to the invention.

FIG. 3 illustrates in more detail an exemplary optical instrument according to the invention. The instrument has a top measurement head 320, which includes components for providing an excitation beam and for detecting emissions from above the sample. The instrument has also an optional bottom measurement head 360, which includes components for providing an excitation beam and for detecting emissions from below the sample. The instrument further comprises a sample platform 380, which has means for moving and a sample tray 389 in order to position successive samples 381 into the measurement volume. There may also be means provided for adjusting the vertical position of the sample platform relative to the top and bottom measurement heads.

The instrument has one or two illumination sources. The main illumination source 312a includes a pulse lamp, and the optical energy of each pulse is preferably equal. The excitation beam generated by the pulse lamp is collimated with a lens 315 and directed through an interference filter 314. The filter is placed on a filter slide, so that the excitation filter to be used in a measurement can be selected from several filters. The excitation beam is then focused to an end of a fibre optic guide 318, which mixes the excitation beam and guides it to an aperture of an optical module 340 according to the invention. The optical module 340 and the lens system 323 directs the excitation beam into the sample 391. The optical module is not described here in more detail because it is explained in relation to other Figures.

The equipment may also include a second pulse lamp 312b, 311b, which may be a low power lamp, e.g. for simultaneous photometric measurements. The instrument has an optical fibre guide 312a for guiding the light from the second lamp. The light can be distributed for the photometric measurement into three filters 314h, 314j and 314k with fibre branches 377h, 377j and 377k.

The light beams are collimated with lenses 375h, 375j and 375k before directing the beams through the filters. The filters can be located on the same or different filter slide as the filter 314e for the first illumination source. If the same filter slide is used for filters of both lamps, the simultaneous measurement modes must be taken into account when the location of the filters is planned. After filtering, the beams are collimated into ends of three optical fibre cables 378, which are led to the bottom measurement head for the photometric measurement. The light beams from the optical cables 378 are focused to three samples 384 with a lens system 379 including lenses for each three beams. After transmitting through the samples the beams are measured with three detectors 322d, 322e and 322f, which are e.g. a photo diodes. The three ends of the fibre optic cables, three lenses, three simultaneously measured samples and three detectors are in this case located in a row perpendicular to the plane of the drawing and thus only one of them can be seen in the drawing.

It is preferable to have a separate optics for the photometrics measurement so that a photoluminescence measurement and a photometrics measurement can be performed simultaneously from different samples. If simultaneous photoluminescence and photometric measurements are required, the analyzer is preferably equipped with two pulse lamps. However, it is also possible to use an instrument with one lamp for photometrics measurements. For example, an optical switch 317 may have an output for an optical fibre 378a, which leads light from the lamp 312a to the photometrics measurement optics 379. It is then possible to control the optical switch either to guide the light for providing excitation for an emission measurement or to guide the light the a photometric measurement.

An optical fibre 318T is used for guiding the excitation beam from the optical switch 317 to the optical module 340 of the top measurement head. An optical fibre 318B is used for guiding the excitation beam from the optical switch 317 to the optical module 350 of the bottom measurement head. The instrument may also have a further lamp so that different lamps can be selected for providing the excitation beam of the top head and the bottom head. In this case, a more versatile optical switch system is required.

The emission beam from the sample 381 is directed with the lens system 323 into the optical module 340 where the emission beam is divided into to two beams. A dichroic mirror in the optical module preferably functions as a filter so that a beam with a wavelength of the first emission is transmitted through the to the first detector 331a, and a beam with a wavelength of the second emission is reflected with the second detector 331b. The detector can be e.g. a photomultiplier tube, which may be used in analogue mode or in photon count mode, or in both modes simultaneously. When the equipment includes two photoluminescence detectors they may be of different types and the detection modes may be different during a measurement.

The first emission beam is collimated with a lens 333a and directed through an interference filter 334j in order to prevent light with a wavelength outside the first emission from passing to the first detector. The first emission beam is then focused with lens 335a to the first detector 331a. The second emission beam is reflected with a mirror 338 to a lens 333b where the beam is collimated and directed through a second interference filter 334k in order to prevent light with a wavelength outside the second emission from passing to the second detector. The second emission beam is then focused with lens 335a to the first detector 331a. The filters 334j and 334k are located on same filter slide or they may locate on different filter slides. The filter slide(s) is movable so that the filters used in the measurement can be selected from a number of filters with different pass-band wavelengths.

In an instrument also comprising a bottom measurement head there are optical switches 337a and 337b for selecting the detected emission beam from the top or bottom measurement head. An optical fibre 338a is used for guiding the first emission beam from the optical module 350 of the bottom measurement head 360 to the optical switch 337a. Another optical fibre 338b is used for guiding the second emission beam from the optical module 350 of the bottom measurement head 360 to the optical switch 337b.

The signals received from the detectors are then amplified and processed to achieve a value for the intensities of the first and second emissions. Measurement signals and reference signals are amplified and read after each excitation pulse and signal corrections are calculated. Basic references are determined with standard solvents after the analyzer has been assembled. If there are more than one excitation pulses used for one well, the corresponding emission signals are digitally integrated.

The instrument has also an optional detector 332c, 331c for chemiluminescence measurements. The detector receives the chemiluminescence radiation from the sample via a thick bundle of optical fibres 318c. It is preferable to have a separate optics for the chemiluminescence measurement so that a photoluminescence measurement and a chemiluminescence measurement can be performed simultaneously from different samples. In FIG. 3 the chemiluminescence measurement is made from a sample located behind sample 381. A photo-multiplier tube can also be used as a detector for the chemiluminescence. The detector can be used in analogue mode or digital mode, or if the properties of the tube allow, both modes may be used simultaneously.

The instrument comprises a carousel wheel 328 for the attachment of optical modules 340a, 340b, . . . The wheel can be rotated around its fixing point 329, and the optical module used in a measurement can thus be selected by controlling the position of the wheel. According to the present invention, the equipment has an optical interface of at least two emission beams and at least one excitation beam for a single optical module.

If the instrument is equipped with a bottom measurement head, there may be a similar optical module 350 used in the bottom measurement head as in the top measurement head. The excitation and emission beams are lead between the two measurement heads with optical fibres 338a, 338b and 318B. There is also a lens system 363 for focusing the beams to the sample and ends of the optical fibres. Since the optical module of the bottom measurement head needs not be so frequently changed, it may be manually changeable. Alternatively a processor-controlled carousel can also be used in the bottom measurement head.

The optical modules are shown essentially enlarged in FIG. 3 in order to better illustrate the optical paths in the instruments. The actual size of the optical modules may be as small as 20 mm×20 mm×20 mm.

The optical modules may be equipped with machine readable codes, such as bar codes, so that the processor of the equipment can check with a code reader, which types of optical modules are installed in each location. This way it can be certified that a correct type of optical module is used for each measurement. The bar code reader or related electronics are not shown in FIG. 3.

The instrument is also equipped with electronics for amplifying and processing the signals from the detectors, as well as electronics for driving the lamp(s). There is also control electronics provided for controlling the measurements, such as selecting filter(s), selecting the optical module(s), controlling optical switch(es), controlling the position of the sample tray 389 for selecting the sample to be measured, and controlling the positions of the measurement heads 320 and 360 relative to the sample platform 380. The electronics is not shown in FIG. 3, as the required electronics can be designed by a skilled person in the art.

In the preferred embodiment the user can adjust various parameters. of a measurement. The excitation pulse energy is adjusted by the discharge voltage and by the capacitors of the flash lamp power supply. Total excitation energy of one measurement is controlled by measuring every pulse and comparing the sum to a reference level of the integrator. The parameters of measurements are preferably user adjustable.

Next some embodiments of possible measurement modes are described referring to FIGS. 4–9. These exemplary embodiments show how the interface for an optical module with apertures gives a possibility for a large variety of different measurement modes. These measurement modes are available with an automatic selection and control of filters, optical switches and just one changeable optical module in each measurement head. The described measurement modes are related but not restricted to photoluminescence measurements.

Figure 4:
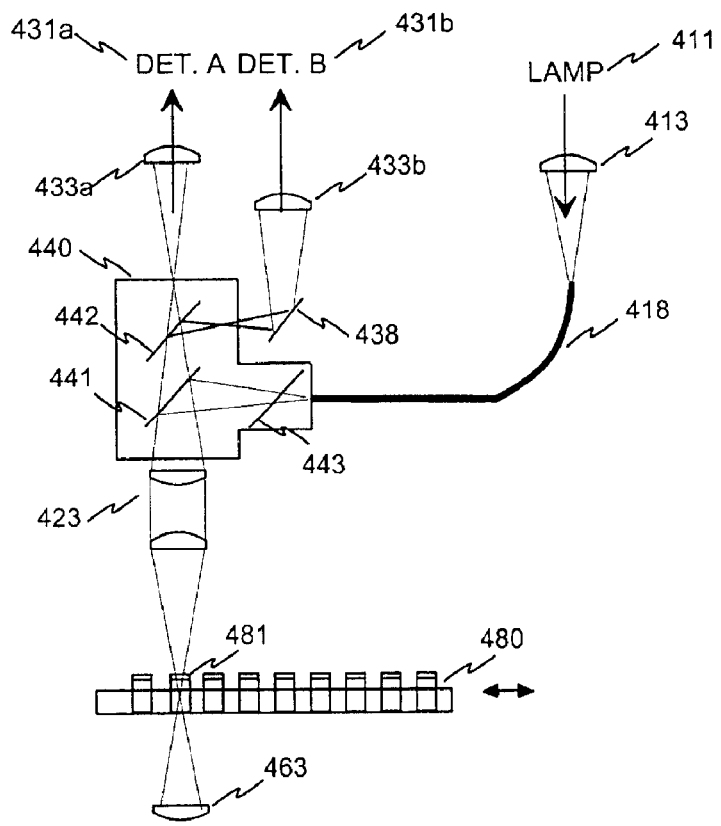
FIG. 4 is a schematic block diagram of an optical unit showing a first embodiment for a double emission measurement according to the invention.

FIG. 4 illustrates a first embodiment of performing a photoluminescence measurement with a measuring instrument according to the present invention. In this embodiment both excitation and detection is made from the above the sample using the top measurement head of the instrument. One of the possible alternative excitation sources 411 gives an excitation pulse, which is guided through an optical system 413 to an optical fibre 418. The optical system may include filters, lenses and mechanical components as was shown in FIG. 3. The excitation beam is mixed in the optical fibre and lead to the optical module 450. The excitation beam is reflected from the mirror 441 and collimated in the optical system 423 into the sample 481 on the sample plate 480 to be measured. The excitation beam provides excitation for two simultaneous measurements.

The excited sample 481 gives two emissions that are measured with detectors A and B. The emission beams are first collimated in the optical system 423, and the beams lead to the optical module 440. The emission beams first transmit the dichroic mirror 441, where after the second dichroic mirror 442 separates the two emission beams. The separation may be based on the wavelength of the emissions, polarization etc. The first emission beam is substantially transmitted through the second dichroic mirror 442 and further collimated and filtered in the optical system 433a to be measured in the detector 431a. The second emission beam is substantially reflected by the second dichroic mirror 442, and further reflected by the mirror 438. The beam is collimated and filtered in the optical system 433b to be measured in the detector 431b.

One advantage of this first embodiment is that the emissions are guided to both detectors directly i.e. without optical fibre cables. This way an optimal sensitivity of the measurement is achieved.

In the first embodiment illustrated in FIG. 4 the whole measurement is made with the top measurement head, and so it is not necessary to have a bottom measurement head in the instrument in order to perform the double emission measurement. The use of an optical module according to the invention gives therefore a possibility to make versatile measurements efficiently even with a basic instrument, which is not equipped with a bottom measurement head. In the further described embodiments for using the instrument according to the invention, also the bottom measurement head is used.

Figure 5:
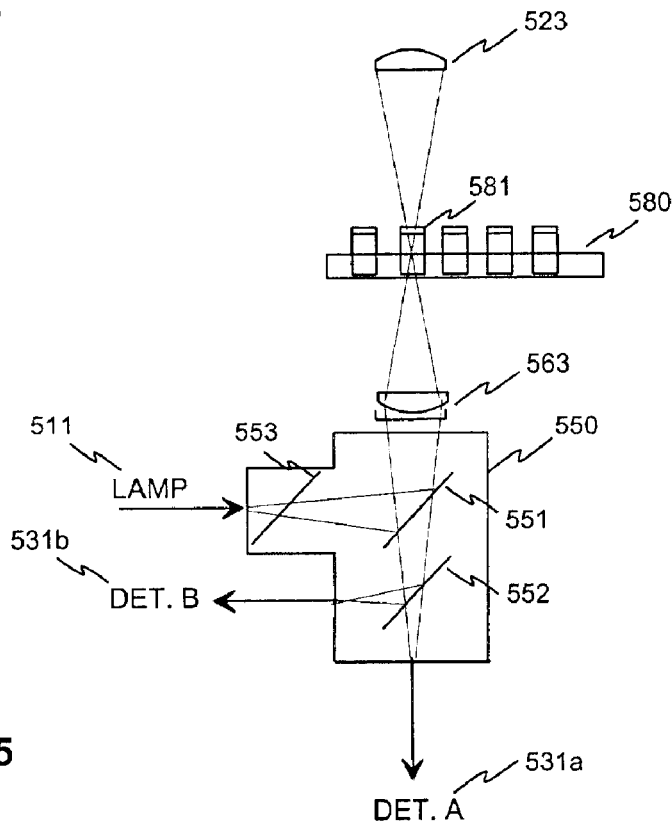
FIG. 5 is a schematic block diagram of an optical unit showing a second embodiment for a double emission measurement according to the invention.

FIG. 5 illustrates a second embodiment of performing a photoluminescence measurement with a measuring instrument according to the present invention. In this embodiment both excitation and detection is made from the below the sample using the bottom measurement head of the instrument. One of the possible alternative excitation sources 511 gives an excitation pulse, which is lead to the optical module of the bottom measurement head with an optical fibre (not shown in the FIG. 5), wherein the excitation beam is mixed. The excitation beam is reflected from the mirror 551 and collimated in the optical system 563 into the sample 581 on the sample plate 580 to be measured. The excitation beam provides excitation for two simultaneous measurements, or alternatively two successive excitations with different wavelengths are made with successive excitation pulses (successive excitation is preferably used only in bottom measurements).

The excited sample 581 gives two emissions that are measured with detectors A and B. The emission beams are first collimated in the optical system 563, and the beams are lead to the optical module 550. The emission beams first transmit the dichroic mirror 551, where after the second dichroic mirror 552 separates the two emission beams. The separation may be based on the wavelength of the emissions, polarization etc. The first emission beam is substantially transmitted through the second dichroic mirror 552 and further lead to the detector 531a through an optical fibre (not shown in FIG. 5). The second emission beam is substantially reflected by the second dichroic mirror 552, and lead to the second detector 531b through an optical fibre (not shown in FIG. 5). The emission beams are then measured in the detectors 531a and 531b.

In the second embodiment illustrated in FIG. 5 the whole measurement is made with the bottom measurement head. This embodiment is useful for making measurements where the substance to be measured lies essentially on the bottom of the sample tube. With this embodiment it is possible to measure simultaneously two emissions from the bottom surface of such substance and thus the measurement can be performed with optimal efficiency. This embodiment also makes it possible to use the top measurement head for a chemiluminescence measurement. This way both the photoluminescence measurement and the chemiluminescence measurement can be performed the samples without changing the locations of the optical modules or cables between the measurements. In the embodiments that are described in the following, both the top measurement head and the bottom measurement head are used for the photoluminescence measurement.

Figure 6:
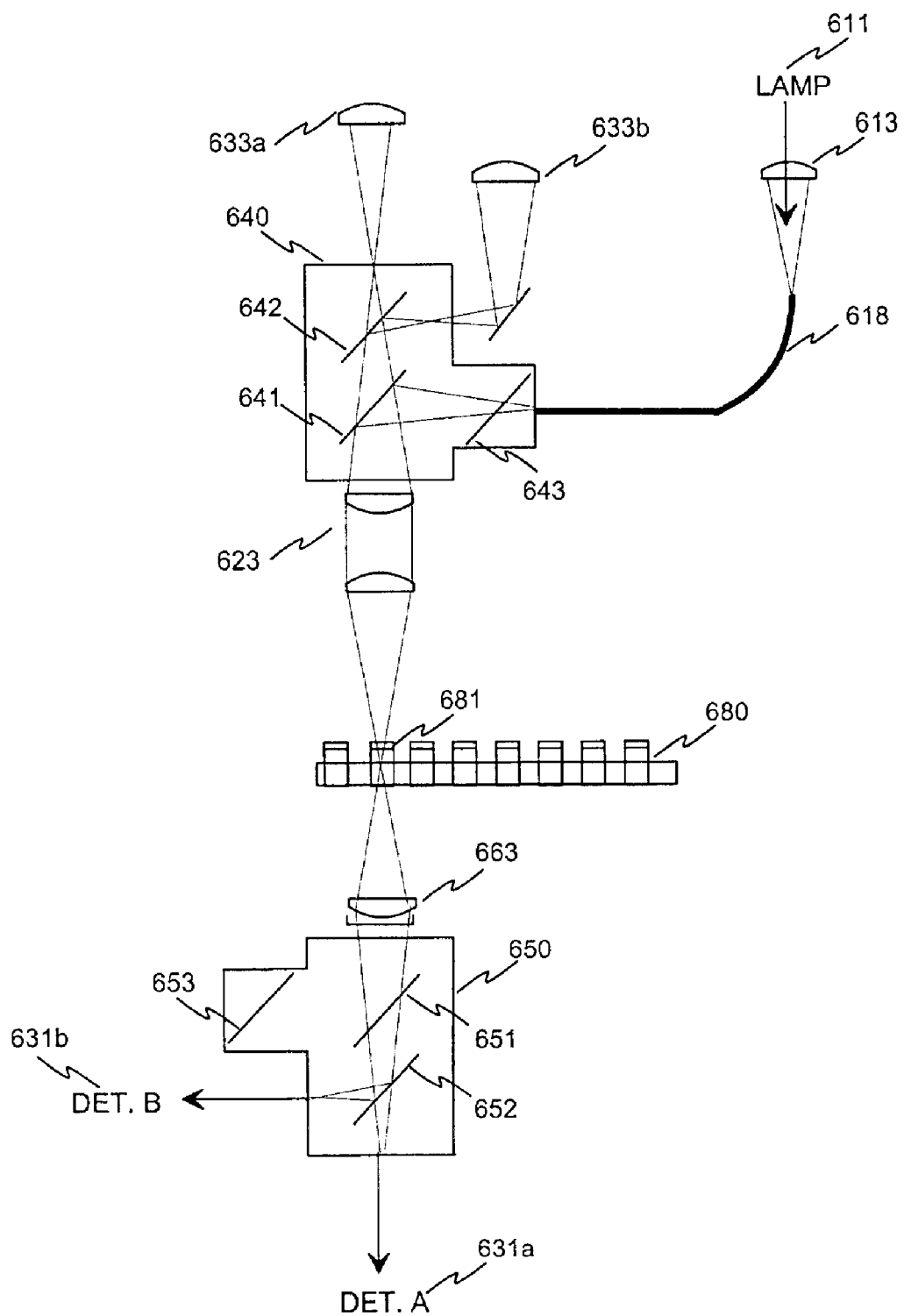
FIG. 6 is a schematic block diagram of an optical unit showing a third embodiment for a double emission measurement according to the invention.

FIG. 6 illustrates a third embodiment of performing a photoluminescence measurement with a measuring instrument according to the present invention. In this embodiment the excitation is made from the above the sample using the top measurement head, and the detection is made from below the sample using the bottom measurement head of the instrument. One of the possible alternative excitation sources 611 gives an excitation pulse, which is guided through an optical system 613 to an optical fibre 618. The optical system may include filters, lenses and mechanical components as was shown in FIG. 3. The excitation beam is mixed in the optical fibre and lead to the optical module 650. The excitation beam is reflected from the mirror 641 and collimated in the optical system 623 into the sample 681 on the sample plate 680 to be measured. The excitation beam provides excitations for two simultaneous measurements.

The excited sample 681 gives two emissions that are measured with detectors A and B. The emission beams are first collimated in the optical system 663, and the beams are lead to the optical module 650 of the bottom measurement head. The emission beams first transmit the dichroic mirror 651, where after the second dichroic mirror 652 separates the two emission beams. The separation may be based on the wavelength of the emissions, polarization etc. The first emission beam is substantially transmitted through the second dichroic mirror 652 and further lead to the detector 631*a* through an optical fibre (not shown in FIG. 6). The second emission beam is substantially reflected by the second dichroic mirror 652, and lead to the second detector 631*b* through an optical fibre (not shown in FIG. 6). The emission beams are then measured in the detectors 631*a* and 631*b*.

The third embodiment illustrated in FIG. 6 gives some advantages compared to the second embodiment of FIG. 5. When the excitation pulse is exposed from the top measurement head the length of the optical fibre within the optical route of the excitation pulse can be made optimally short. This way the attenuation of the optical fibre can be minimized, and consequently a maximum illumination intensity is achieved.

Another advantage of the embodiment of FIG. 6 is that it is possible to use an optical module where there is no first mirror 651 in the module. This way the attenuation of the emission beam caused by the excitation mirror 651 can be totally avoided.

Figure 7:
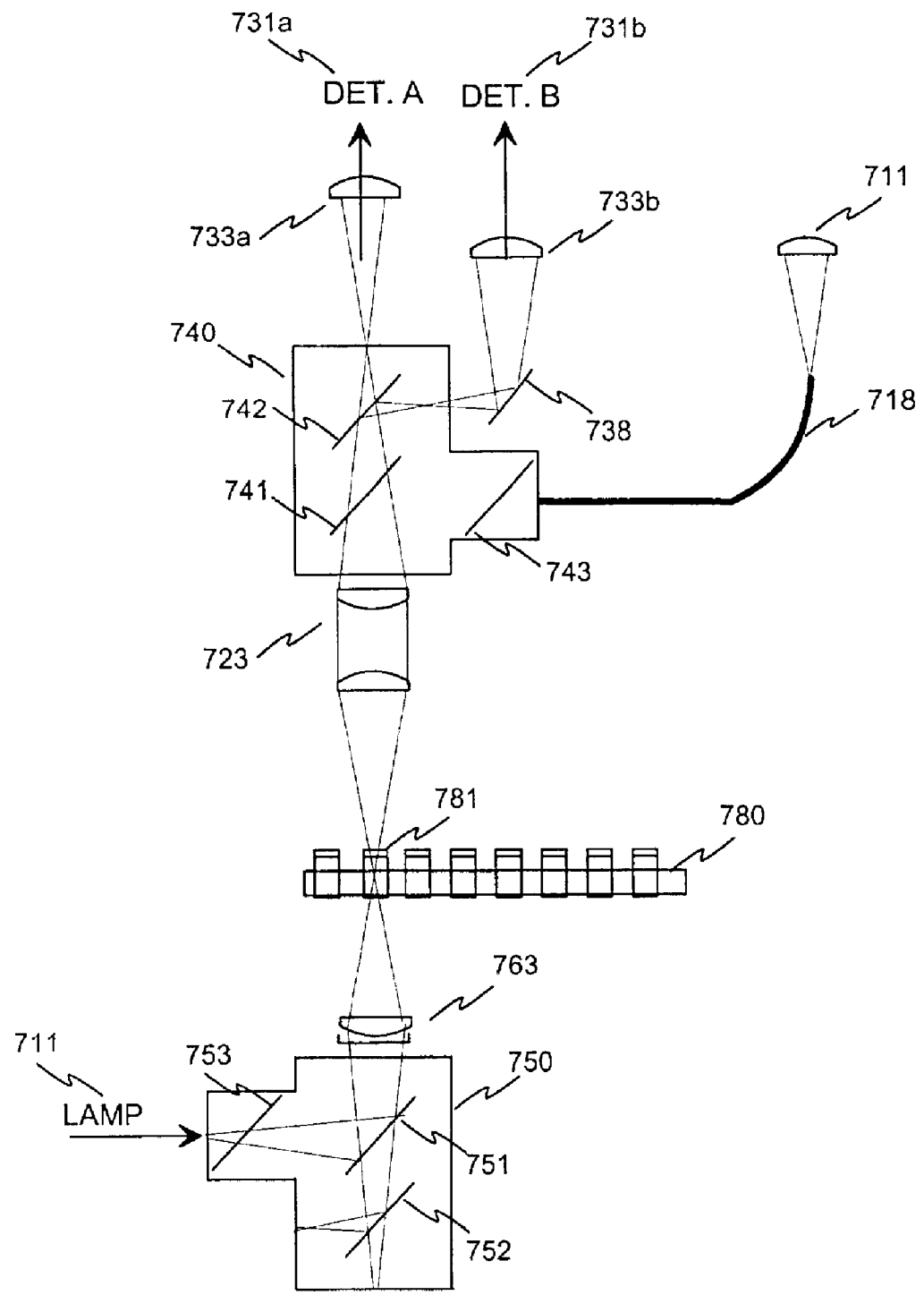
FIG. 7 is a schematic block diagram of an optical unit showing a fourth embodiment for a double emission measurement according to the invention.

FIG. 7 illustrates a fourth embodiment of performing a photoluminescence measurement with a measuring instrument according to the present invention. In this embodiment the excitation is made from below the sample using the bottom measurement head, and the detection is made from above the sample using the top measurement head of the instrument. One of the possible alternative excitation sources 711 gives an excitation pulse, which is lead to the optical module of the bottom measurement head with an optical fibre (not shown in the FIG. 7), wherein the excitation beam is mixed. The excitation beam is reflected from the mirror 751 and collimated in the optical system 763 into the sample 781 on the sample plate 780 to be measured. The excitation beam provides excitation for two simultaneous measurements.

The excited sample 781 gives two emissions that are measured with detectors A and B. The emission beams are first collimated in the optical system 723, and the beams lead to the optical module 740. The emission beams first transmit the dichroic mirror 741, where after the second dichroic mirror 742 separates the two emission beams. The separation may be based on the wavelength of the emissions, polarization etc. The first emission beam is substantially transmitted through the second dichroic mirror 742 and further collimated and filtered in the optical system 733*a* to be measured in the detector 731*a*. The second emission beam is substantially reflected by the second dichroic mirror 742, and further reflected by the mirror 738. The beam is collimated and filtered in the optical system 733*b* to be measured in the detector 731*b*.

The fourth embodiment illustrated in FIG. 7 gives some advantages compared to the first embodiment of FIG. 4. When the excitation beam is exposed from the bottom measurement head it is possible to use in the top measurement head an optical module where there is no first mirror 741 in the module. This way the attenuation of the emission beam caused by the excitation mirror 741 can be totally avoided.

Figure 8:
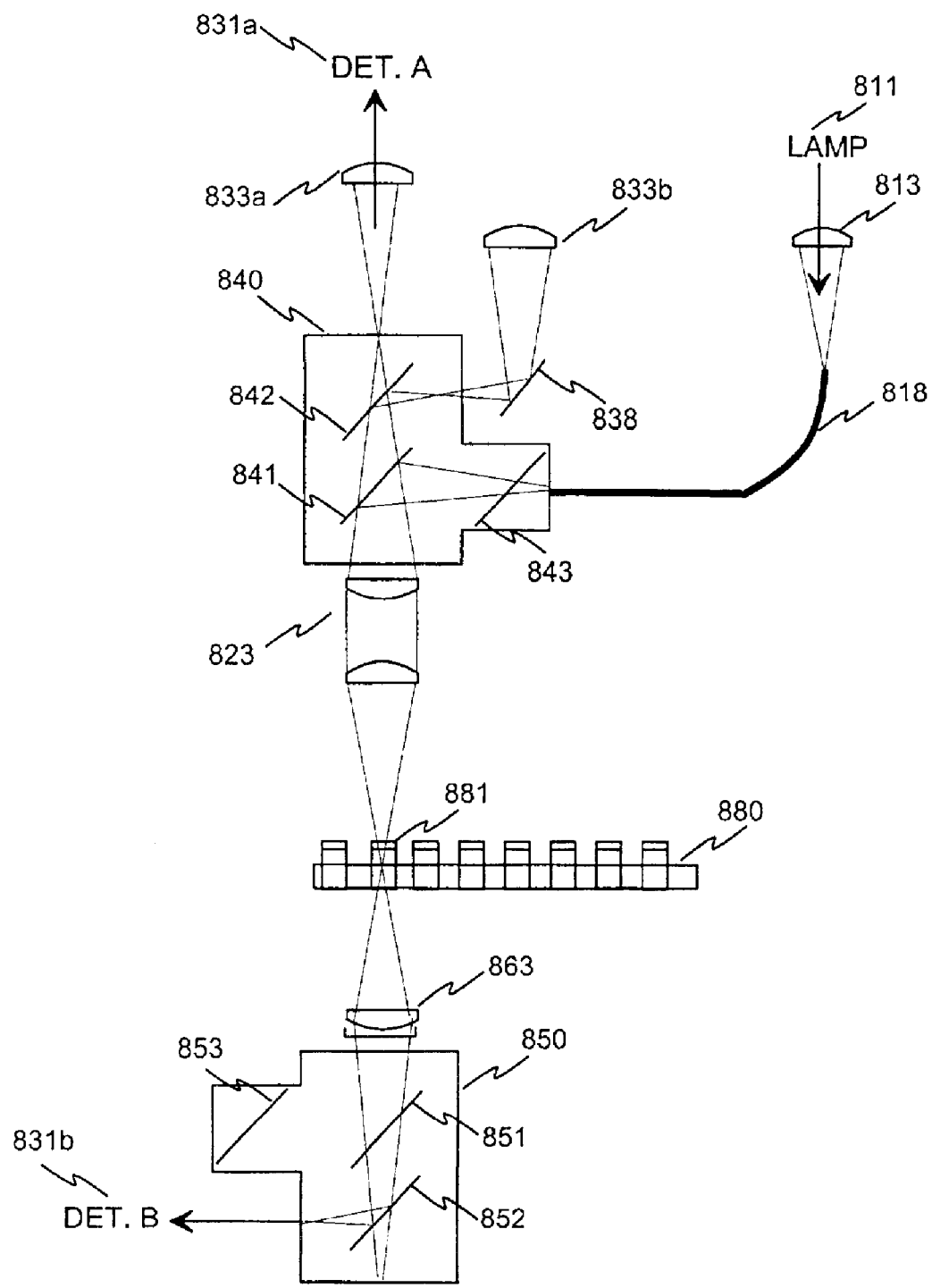
FIG. 8 is a schematic block diagram of an optical unit showing a fifth embodiment for a double emission measurement according to the invention.

FIG. 8 illustrates a fifth embodiment of performing a photoluminescence measurement with a measuring instrument according to the present invention. In this embodiment the excitation is made from the above the sample using the top measurement head. The detection if the first emission is made from above the sample using the top measurement head, and the detection of the second emission is made from below the sample using the bottom measurement head of the instrument.

One of the possible alternative excitation sources 811 gives an excitation pulse, which is guided through an optical system 813 to an optical fibre 818. The optical system may include filters, lenses and mechanical components as was shown in FIG. 3. The excitation beam is mixed in the optical fibre and lead to the optical module 850. The excitation beam is reflected from the mirror 841 and collimated in the optical system 823 into the sample 881 on the sample plate 880 to be measured.

The excitation beam provides excitations for two simultaneous measurements. The excited sample 881 gives two emissions that are measured with detectors A and B. The first emission beam is first collimated in the optical system 823 and lead to the optical module 840 of the top measurement head. The first emission beam is substantially transmitted by the first dichroic mirror 841 and the second dichroic mirror 842. The first emission beam is then collimated and filtered in the optical system 833*a* to be measured in the detector 831*a*.

The second emission beam is first collimated in the optical system 863, and the beam is lead to the optical module 850 of the bottom measurement head. The emission beam first transmits the dichroic mirror 651, where after it is substantially reflected in the second dichroic mirror 852. The second emission beam is lead to the second detector 831*b* through an optical fibre (not shown in FIG. 6). The emission beams are then measured in the detectors 831*a* and 831*b*.

One advantage of the embodiment of FIG. 8 is that it is possible to measure simultaneously emissions from both above and below the sample simultaneously.

There is also another advantage related to the embodiment illustrated in FIG. 8. When the two emissions are measured with different measurement heads it allows the use of only one mirror within the path of the emission beam. In the top measurement head it is possible to use an optical module, which has no second mirror 842. In the bottom measurement head it is possible to use an optical module, which has no first mirror 851. It is also possible to use a non-dichroic mirror 852 in the bottom measurement head. This way a very small attenuation is achieved in the measurement of the both emissions. Especially the measurement of the first emission can be measured with high sensitivity, because of the direct optical path between the sample and the detector 831a.

Figure 9:
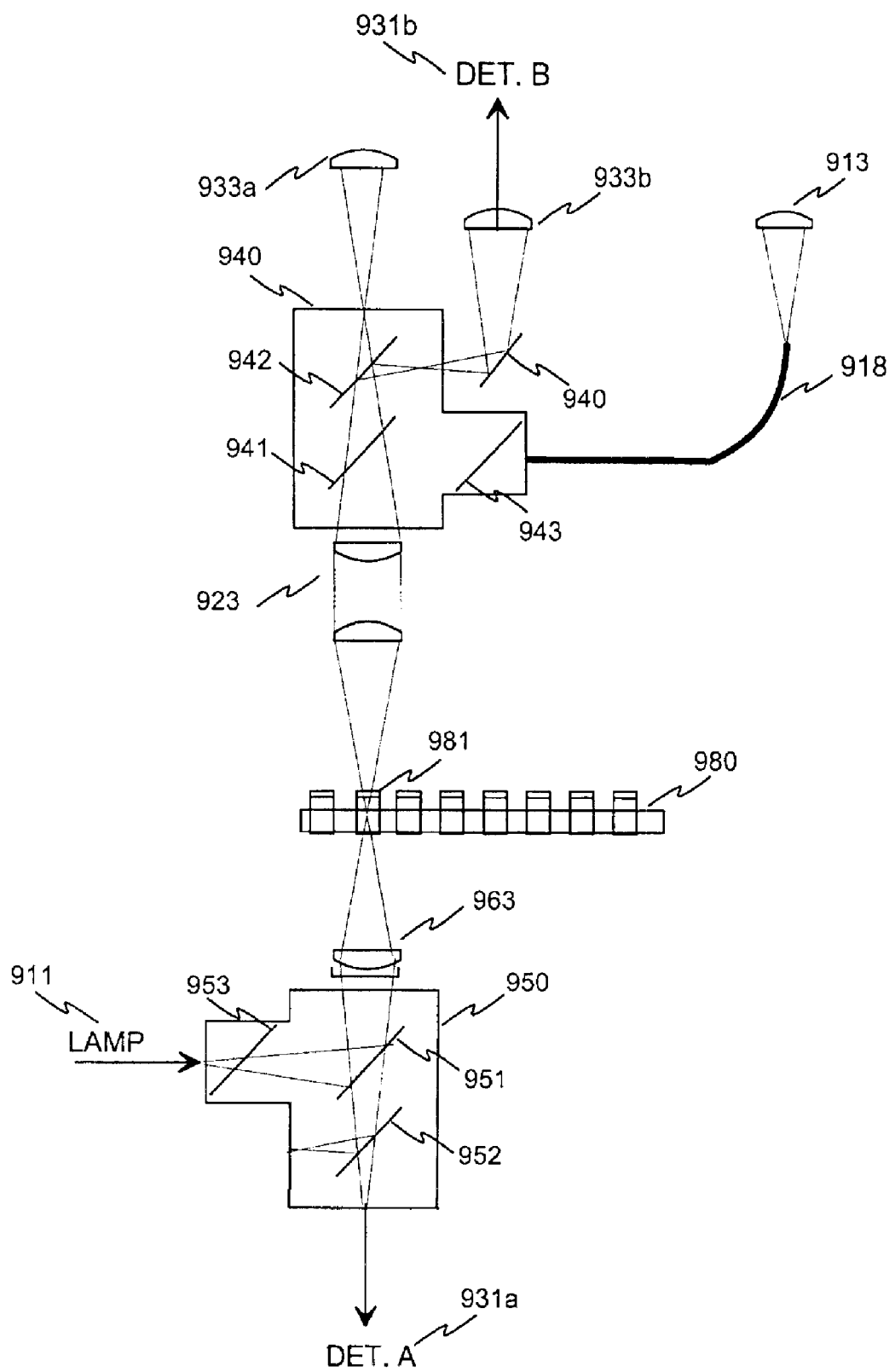
FIG. 9 is a schematic block diagram of an optical unit showing a sixth embodiment for a double emission measurement according to the invention.

FIG. 9 illustrates a sixth embodiment of performing a photoluminescence measurement with a measuring instrument according to the present invention. In this embodiment the excitation is made from below the sample using the bottom measurement head. The detection of the first emission is made from below the sample using the bottom measurement head, and the detection of the second emission is made from above the sample using the top measurement head of the instrument.

One of the possible alternative excitation sources 911 gives an excitation pulse, which is lead to the optical module of the bottom measurement head with an optical fibre (not shown in the FIG. 9), wherein the excitation beam is mixed. The excitation beam is reflected from the mirror 951 and collimated in the optical system 963 into the sample 981 on the sample plate 980 to be measured. The excitation beam provides excitation for two simultaneous measurements.

The excited sample 981 gives two emissions that are measured with detectors A and B. The first emission beam is first collimated in the optical system 963, and the beam is lead to the optical module 950 of the bottom measurement head. The first emission beam is substantially transmitted by the first dichroic mirror 951 and the second dichroic mirror 952. The first emission beam is further lead to the detector 831a through an optical fibre (not shown in FIG. 9). The first emission beam is finally measured in the detector 931a.

The second emission beam is first collimated in the optical system 923, and lead to the optical module 940. The second emission beam first transmits the dichroic mirror 941, where after the second emission beam is substantially reflected by the second dichroic mirror 942, and further reflected by the mirror 938. The second emission beam is collimated and filtered in the optical system 933b and measured in the detector 931b.

Also the embodiment of FIG. 9 has the advantage that it is possible to measure simultaneously emissions from both above and below the sample simultaneously.

There is also another advantage related to the embodiment illustrated in FIG. 9. When the two emissions are measured with different measurement heads it allows the use of only one mirror within the path of the emission beam. In the top measurement head it is possible to use an optical module, which has no first mirror 941. In the bottom measurement head it is possible to use an optical module, which has no second mirror 952. It is also possible to use a non-dichroic mirror 941 in the top measurement head. This way a very small attenuation is achieved in the measurement of both emissions.

Figure 10:
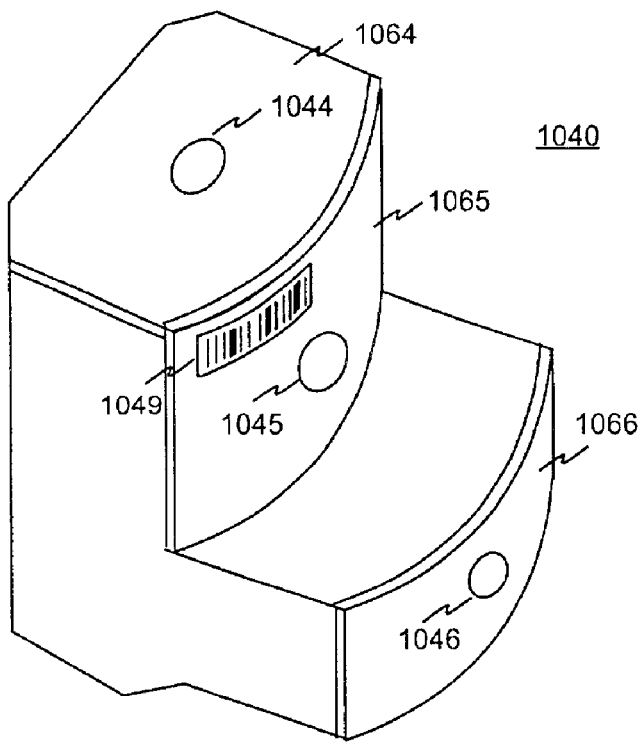
FIG. 10 illustrates a perspective view of an exemplary top optical module according to the invention.

FIG. 10 illustrates a perspective view of an exemplary optical module 1040 according to the invention. It is designed for a top measurement head, but it is also possible to design a bottom measurement head, which is adapted for such a module. The Figure shows an aperture 1046 for the excitation beam from the lamp, an aperture 1044 for the emission beam to the first detector and an aperture for the emission beam to the second detector. In this case, the apertures of the optical module can be changed by changing the respective wall 1064, 1065 or 1066 of the optical module. The walls can be attached by e.g. screws (not shown in FIG. 10). There is also a bar code 1049 shown on the optical cube for a possible automatic recognition of the module type.

Figure 11:
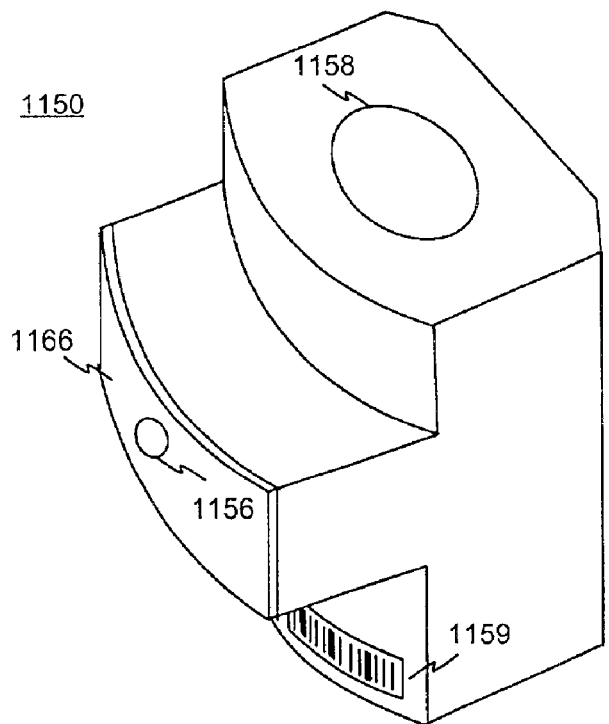
FIG. 11 illustrates a perspective view of an exemplary bottom optical module according to the invention.

FIG. 11 illustrates a perspective view of another exemplary optical module 1150 according to the invention. It is designed for a bottom measurement head, but it is also possible to design top and bottom measurement heads, which are adapted for similar modules. The Figure shows an aperture 1156 for the excitation beam from the lamp, and an aperture 1158 for providing an optical interface to the sample. In this case, aperture 1156 of the optical module can be changed by changing the respective wall 1166 of the optical module. The wall can be attached by e.g. screws (not shown in FIG. 11). There is also a bar code 1159 shown on the optical cube for a possible automatic recognition of the module type.

Figure 12:
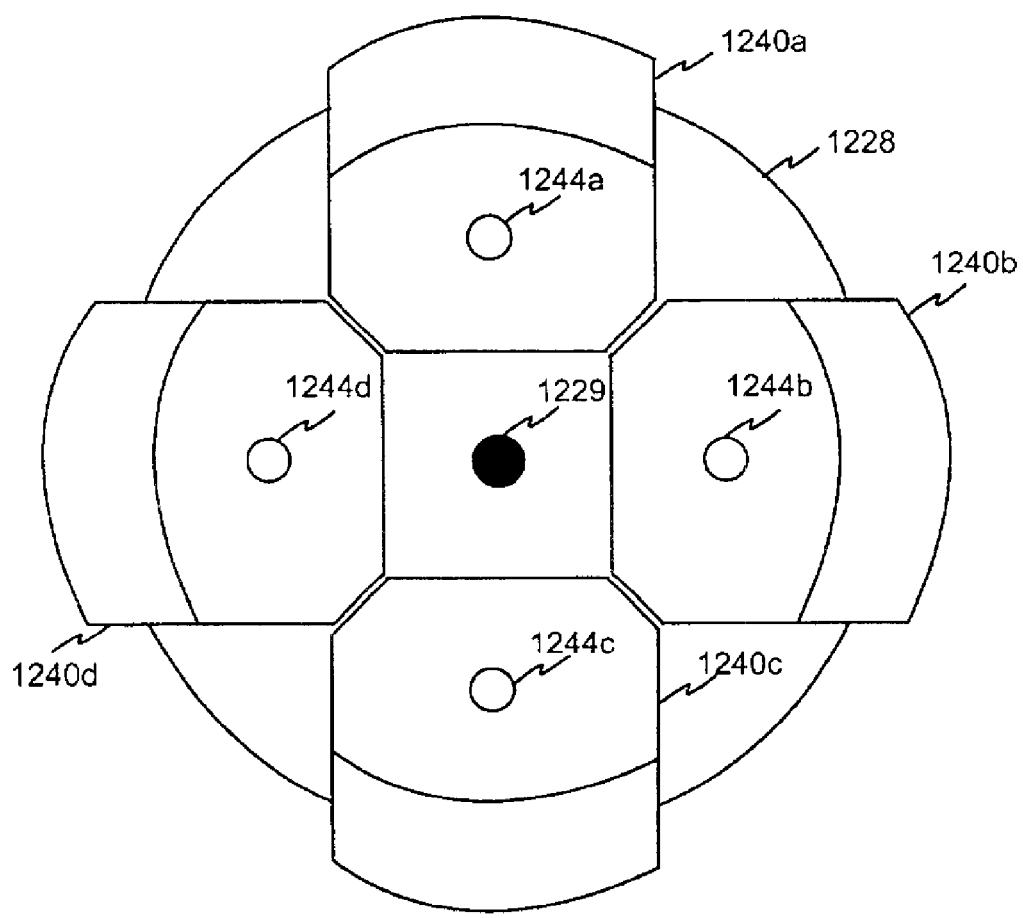
FIG. 12 illustrates an exemplary four-position wheel with four optical modules according to the invention.

FIG. 12 illustrates a top view of an exemplary arrangement where four optical modules are attached to a carousel 1228 in a top measurement head. The optical modules are cited 1240a, 1240b, 1240c and 1240d with their apertures for the emission to the first detector cited as 1244a, 1244b, 1244c and 1244d. The instrument preferably has means for turning the carousel around its axis 1229 so the one of the four optical modules can be selected for use by the program of the instrument. If the optical modules are equipped with a code, such as bar code, the control unit of the instrument may check, which modules are available in each position of the carousel. It is preferable that there is an attachment arrangement for the optical modules, which allows the optical modules be easily removed and attached when necessary. Although the carousel of FIG. 12 is designed for a top measurement head, a bottom measurement head may of course also be equipped with such a carousel for an automatically controlled change of the optical module. Although there are four optical modules shown in FIG. 12, there may naturally be a different number of optical modules. Considering the preferable small size of the optical modules, it is possible to provide a carousel with e.g. 8 or 16 optical modules.

It is also possible to use another kind of mechanical arrangement for the optical modules instead of a carousel. For example, there may be a slide for the optical modules, wherein the optical modules are placed parallel in a line, and a module to be used can be changed by shifting the slide into a corresponding position. If a slide is used, there may be slides of different lengths with a different number on locations for optical modules.

In the following some embodiments of possible optical modules are described referring to FIGS. 13–22. These exemplary embodiments show optical modules, which can be used in an optical instrument according to the invention including an interface for receiving two emissions from an optical module. These optical modules can also be used for implementing the measurement modes described in FIGS. 4–9, and generally for implementing the process and method according to the invention.

FIG. 13 illustrates a cross section view from the side of an exemplary optical module for a top measurement head. This optical module 1340 comprises three dichroic mirrors. The module receives an excitation beam from the aperture 1346, and mirror 1343 reflects a part of the excitation beam into a reference sensor through the aperture 1347. The main part of the excitation beam is reflected from the mirror 1341 and thus directed to a sample through the aperture 1348.

The emission from the sample is received into the module through the aperture 1348. The emissions transmit the dichroic mirror 1341 and reach the further dichroic mirror 1342. The mirror 1342 splits the emission beam into a first beam that is led to the first detector through the aperture 1344, and a second beam that is led to the second detector through the aperture 1345.

The optical module illustrated in FIG. 13 is very suitable for the double emission measurement, which was described in FIG. 4. However, this optical module can be used also in many other types of measurements, such as those described in FIGS. 6–9 or single emission measurements, if an optimized performance is not required.

FIG. 14 illustrates a cross section view from the side of another exemplary optical module for a top measurement head. This optical module 1440 comprises one dichroic mirror 1443 and one non-dichroic mirror 1441. The module receives an excitation beam from the aperture 1446, and mirror 1443 reflects a part of the excitation beam into a reference sensor through the aperture 1447. The main part of the excitation beam is reflected from the mirror 1441 and thus directed to a sample through the aperture 1448.

This optical module is designed for measurements where emission measurement is made using the bottom measurement head. The measurement illustrated in FIG. 6 is an example of such a measurement. Therefore this optical module for the top measurement head does not have any optical paths for emission beams. One advantage of this optical module is that attenuation of the excitation beam is minimal.

FIG. 15 illustrates a cross section view from the side of a third exemplary optical module for a top measurement head. This optical module 1540 comprises one dichroic mirror. This optical module is designed for measurements where bottom measurement head is used for excitation. An example of this kind of measurement is illustrated in FIG. 7. Therefore this optical module does not have any optical paths for an excitation beam.

The emission from the sample is received into the module through the aperture 1548. The mirror 1542 splits the emission beam into a first beam that is led to the first detector through the aperture 1544, and a second beam that is led to the second detector through the aperture 1545.

Although this optical module illustrated in FIG. 15 is very suitable for the double emission measurement, which was described in FIG. 7, this optical module can also be used in many other types of measurements, such as single emission measurements, if an optimized performance is not required.

FIG. 16 illustrates a cross section view from the side of a fourth exemplary optical module for a top measurement head. This optical module 1640 comprises two dichroic mirrors. The module receives an excitation beam from the aperture 1646, and mirror 1643 reflects a part of the excitation beam into a reference sensor through the aperture 1647. The main part of the excitation beam is reflected from the mirror 1641 and thus directed to a sample through the aperture 1648.

The emission from the sample is received into the module through the aperture 1648. The emission transmits the dichroic mirror 1641, and it is led to the first detector through the aperture 1644.

The optical module illustrated in FIG. 16 is very suitable for a double emission measurement, where the first emission is measured with the top measurement head and the second emission is measured with the bottom measurement head. This kind of measurement was described in FIG. 8. However, this optical module can be used also in many other types of measurements, such as single emission measurements.

FIG. 17 illustrates a cross section view from the side of a fifth exemplary optical module for a top measurement head. This optical module 1740 comprises one non-dichroic mirror. This optical module is designed for measurements where excitation is made using the bottom measurement head. An example of this kind of measurement is illustrated in FIG. 9. Therefore this optical module does not have any optical paths for an excitation beam.

The emission from the sample is received into the module through the aperture 1748. The mirror 1742 reflects the emission beam, which is further led to the second detector through the aperture 1745.

The optical module illustrated in FIG. 17 is very suitable for a double emission measurement, where the second emission is measured with the top measurement head and the first emission is measured with the bottom measurement head. This kind of measurement was described in FIG. 9. However, this optical module can be used also in many other types of measurements, if an optimised performance is not required.

Although the optical modules illustrated in FIGS. 13–17 are designed for the top measurement head, it is also possible to design the bottom measurement head be adapted to the use of these modules.

Figure 18:
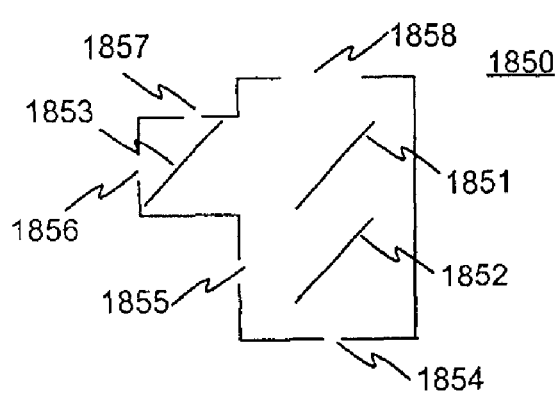
FIG. 18 illustrates a first exemplary bottom head optical module according to the invention for implementing the invention.

FIG. 18 illustrates a cross section view from the side of an exemplary optical module for a bottom measurement head. This optical module 1850 comprises three mirrors. The module receives an excitation beam from the aperture 1856, and mirror 1853 reflects a part of the excitation beam into a reference sensor through the aperture 1857. The main part of the excitation beam is reflected from the mirror 1851 and thus directed to a sample through the aperture 1858.

The emissions from the sample are received into the module through the aperture 1858. The emissions transmit the dichroic mirror 1851 and reach the further dichroic mirror 1852. The mirror 1852 splits the emission beam into a first beam that is led to the first detector through the aperture 1854, and a second beam that is led to the second detector through the aperture 1855.

The optical module illustrated in FIG. 18 is very suitable for the double emission measurement, which was described in FIG. 5. However, this optical module can be used also in many other types of measurements, such as those described in FIGS. 6–9 or single emission measurements, if an optimized performance is not required.

Figure 19:
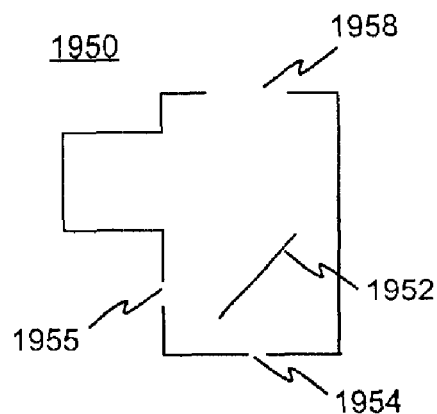
FIG. 19 illustrates a second exemplary bottom head optical module for implementing the invention.

FIG. 19 illustrates a cross section view from the side of another exemplary optical module for a bottom measurement head. This optical module 1950 comprises one dichroic mirror. This optical module is designed for measurements where excitation is made using the top measurement head. An example of this kind of measurement is illustrated in FIG. 6. Therefore this optical module does not have any optical paths for an excitation beam.

The emissions from the sample are received into the module through the aperture 1958. The mirror 1952 splits the emission beam into a first beam that is led to the first detector through the aperture 1954, and a second beam that is led to the second detector through the aperture 1955.

Although this optical module illustrated in FIG. 19 is very suitable for the double emission measurement, which was described in FIG. 6, this optical module can also be used in many other types of measurements, such as single emission measurements, if an optimized performance is not required.

Figure 20:
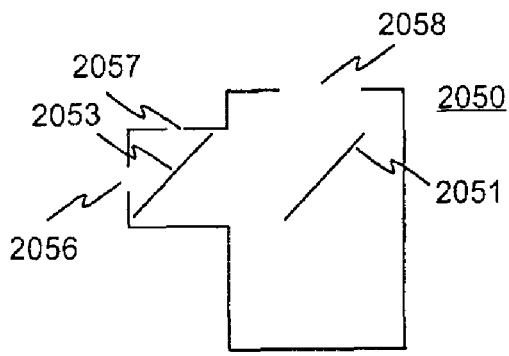
FIG. 20 illustrates a third exemplary bottom head optical module for implementing the invention.

FIG. 20 illustrates a cross section view from the side of a third exemplary optical module for a bottom measurement head. This optical module 2050 comprises one beam splitter mirror 2053 and one further mirror 2051. The module receives an excitation beam from the aperture 2056, and mirror 2053 reflects a part of the excitation beam into a reference sensor through the aperture 2057. The main part of the excitation beam is reflected from the mirror 2051 and thus directed to a sample through the aperture 2058.

This optical module is designed for measurements where emission measurement is made using the top measurement head. The measurement illustrated in FIG. 7 is an example of such a measurement. Therefore this optical module designed for the bottom measurement head does not have any optical paths for emission beams. One advantage of this optical module is that attenuation of the excitation beam is small.

Figure 21:
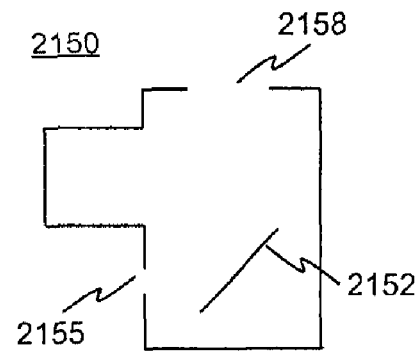
FIG. 21 illustrates a fourth exemplary bottom head optical module for implementing the invention.

FIG. 21 illustrates a cross section view from the side of a fourth exemplary optical module for a bottom measurement head. This optical module 2150 comprises one non-dichroic mirror. This optical module is designed for measurements where excitation is made using the top measurement head. An example of this kind of measurement is illustrated in FIG. 8. Therefore this optical module does not have any optical paths for an excitation beam.

The emission from the sample is received into the module through the aperture 2158. The mirror 2152 reflects the emission beam, which is further led to the second detector through the aperture 2155.

The optical module illustrated in FIG. 21 is very suitable for a double emission measurement, where the second emission is measured with the bottom measurement head and the first emission is measured with the top measurement head. This kind of measurement was described in FIG. 8. However, this optical module can be used also in other types of measurements, if an optimised performance is not required.

Figure 22:
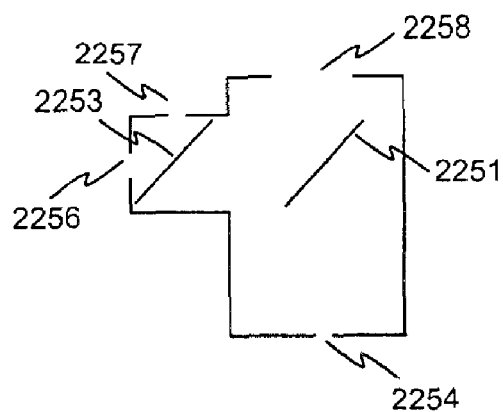
FIG. 22 illustrates a fifth exemplary bottom head optical module for implementing the invention.

FIG. 22 illustrates a cross section view from the side of a fifth exemplary optical module for a bottom measurement head. This optical module 2250 comprises two dicroic mirrors. The module receives an excitation beam from the aperture 2256, and mirror 2253 reflects a part of the excitation beam into a reference sensor through the aperture 2257. The main part of the excitation beam is reflected from the mirror 2251 and thus directed to a sample through the aperture 2258.

The emission from the sample is received into the module through the aperture 2258. The emission transmits the dichroic mirror 2251, and it is led to the first detector through the aperture 2254.

The optical module illustrated in FIG. 22 is very suitable for a double emission measurement, where the first emission is measured with the bottom measurement head and the second emission is measured with the top measurement head. This kind of measurement was described in FIG. 9. However, this optical module can be used also in many other types of measurements, such as single emission measurements.

Although the optical modules illustrated in FIGS. 18–22 are designed for the bottom measurement head, it is also possible to design both the top measurement head and the bottom measurement head be adapted to the use of these modules.

Figure 23:
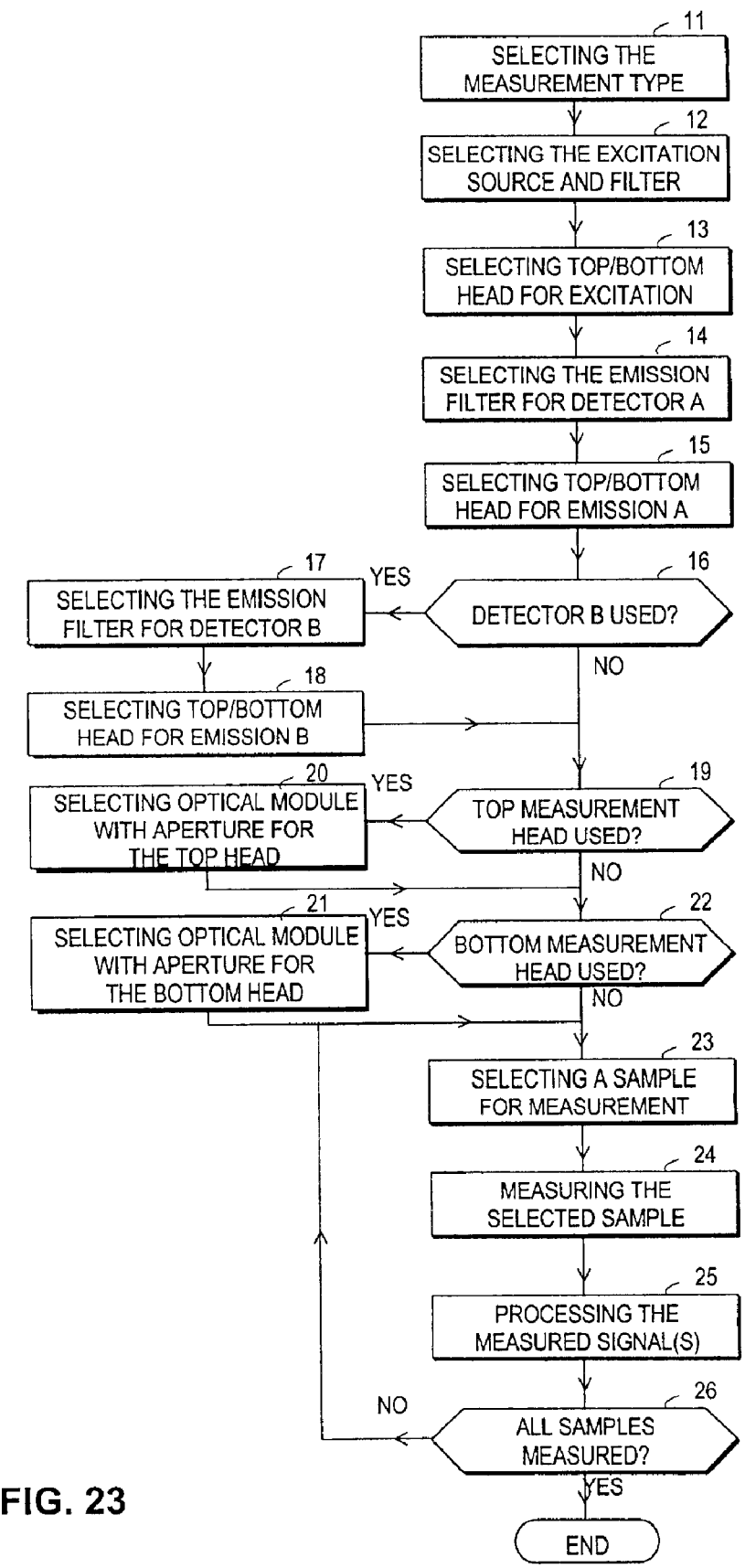
FIG. 23 illustrates an exemplary process for performing a measurement with an optical measurement instrument according to the invention.

FIG. 23 illustrates a flow diagram of an exemplary process according to the invention for using an optical instrument for a photoluminescence measurement. In phase 11 the type of measurement is selected. The excitation source and interference filter is then selected according to the measurement type in phase 12. Either the top measurement head or bottom measurement head is selected for providing the excitation beam into the sample, phase 13. This is made e.g. with an optical switch.

In phase 14, the emission filter is selected for the detector A. Either the top measurement head or the bottom measurement head is then selected in step 15 for receiving the emission A and for guiding the emission beam A into the detector A. The optical path is connected to the selected measurement head e.g. by controlling an optical switch. If two emissions are measured the emission filter is also selected for the detector B, steps 16 and 17, and either the top measurement head or the bottom measurement head is selected in step 18 for receiving the emission B and guiding the emission beam into the detector B. The optical path can be connected to the selected measurement head also by controlling an optical switch.

If excitation or emission of the measurement is made from above the sample, i.e. the top measurement head is used, then the optical module of the top measurement head is selected and placed into the measurement location, phases 19 and 20. If excitation or emission of the measurement is made from below the sample, i.e. the bottom measurement head is used, then the optical module of the bottom measurement head is selected and placed into the measurement location, phases 21 and 22. According to the invention, an optical module with aperture(s) for receiving an excitation beam or outputting an emission beam is selected to either top or bottom measurement head. Especially, if the same measurement head is used for receiving two emissions, an optical module with an aperture output for both detectors is preferably selected in the measurement head.

After the optical paths have been selected, the first sample to be measured is selected, phase 23. The selected sample is then measured, 24, and the signals received from the detector(s) are processed to produce measurement result(s) for the measured sample, phase 25. Samples are successively measured by repeating phases 23–26 until all samples have been measured.

One should note that several variations of the measurement process according to the invention can be applied. For example, the order of the process phases can be different from the one described above. Also, if an instrument without a bottom measurement head is used, the selection between top/bottom measurement head or selection of the optical module for the bottom measurement head are not required. And if only one excitation source is available, a selection between excitation sources is not required.

Figure 24:
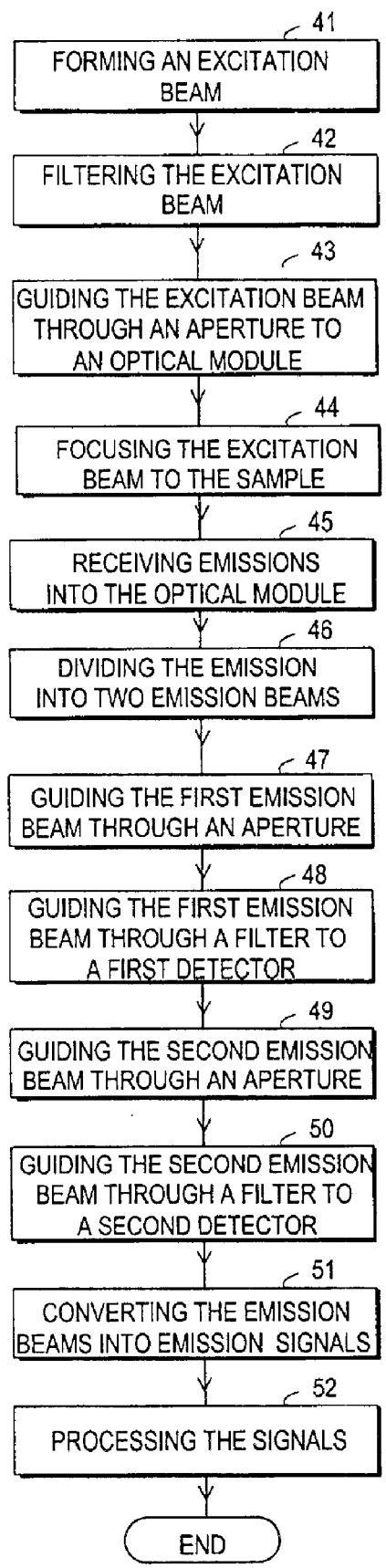
FIG. 24 illustrates an exemplary method for performing a measurement according to the invention.

FIG. 24 illustrates a flow diagram of an exemplary method according to the invention for optical measurement of a sample. In phase 41 an excitation beam is formed in an illumination source, and the excitation beam is filtered with an interference filter in phase 42 to include wavelength(s) for the excitation of two substances in the sample. The filtered excitation beam is guided through a small aperture to an optical module according to the invention, wherein the beam is reflected, phase 43. The excitation beam is then focused into the sample within a volume that is to be measured, 44. The excitation beam may be an excitation pulse, succession of pulses or a continuous wave beam, depending on the type of measurement.

After the (fluorescent) label substances in the sample have been excited, they release emissions, which are received into the optical module according to the invention, phase 45. The emissions may be in the form of bursts or continuous emissions depending on the excitation. In the optical module the emission beam may first transmit an excitation mirror, and the emission beams are then divided with a dichroic mirror into two emission beams e.g. according to their wavelength in phase 46. The splitting may be performed in same optical module.

The first emission beam received from the first substance of the sample is first guided (focused) through an aperture of the optical module, 47. The beam is then filtered in by transmitting the first emission beam and blocking other light, e.g. light with different wavelength, and finally the first emission beam is then guided to a first detector, phase 48. Simultaneously with receiving the first emission, the second emission beam is received from the second substance of the sample, guided through the optical module and focused through an aperture of the optical module, 49. The beam is then filtered by transmitting the second emission beam and blocking other light, e.g. light with different wavelength, and the filtered second emission is then guided to a second detector, phase 50. The emissions are then converted into electrical signals in the detectors, phase 51, and the signals are processed in order to provide measurement results showing the quantity of the first and second substances within the sample, phase 52.

One should note that the inventive method is not restricted to the measurement of two emissions of two substances, but there may be further means for splitting the emission into several emission beams and further detectors for measuring the emission beams.

Above, examples of a general measurement process and method were described. Next some typical measurements are described in more detail. In this description the use of an optical instrument according to FIG. 3 is referred to.

FI and TRF Measurements

In a prompt photoluminescence, i.e. FI measurement, one excitation pulse is given for each sample to be measured. In a FI measurement an excitation filter and an emission filter are selected as was described above. A suitable optical module is also selected; the optical module may be a general-purpose module, or it may be a module that is especially designed for a determined label substance.

After a sample has been chosen for the measurement an excitation pulse is transmitted, and reference $R_1$ is read wherein $R_i$ is the amount of light that has been used in the excitation of the label. The illumination reference is received from a reference detector 319. Emission signals $S1_A$ and $S1_B$ are then read from the detectors. A correction factor for the signals is calculated on the basis of the illumination reference value. The long-term stability of the equipment is fixed to this amount of light when using a determined excitation filter and mirror block.

If several excitation pulses are used for one sample, the sequence is repeated and the results are summed or averaged. This leads to improved signal-to-noise ratio of the measurement.

A time resolved photoluminescence measurement, i.e. TRF measurement, is equal to the FI measurement except that several excitation pulses are formed for each sample and corresponding emissions are measured. The measurement signals and reference signals are read after each excitation pulse and signal corrections are calculated. Basic references are determined with standard solvents after the analyzer has been assembled. After receiving all emission signals from a sample, the results are preferably digitally integrated. Finally, a linear correction can be made for the digital signal using a reference.

Chemiluminescence Measurement

In a chemiluminescence measurement no excitation pulse is given. A separate detector can be used for the chemiluminescence measurement, if it is desirable to make chemiluminescence measurements simultaneously with a photoluminescence measurement. In this case the simultaneous chemiluminescence and photoluminescence measurements are made from different samples. However, if a simultaneous measurement is not required, same detector as used for photoluminescence measurements can be used for the chemiluminescence measurement.

An emission filter is not needed in a chemiluminescence measurement, so the filter slide can be moved outside the measurement beam. An optical module is selected according to the label; a TR module can be used, but a better measurement quality can be achieved with a block designed for the chemiluminescence measurement. The analogue gates or a digital window for the measurement period is set. After a sample is chosen a first period for measuring illumination is triggered. The length of the measurement period is e.g. 1 ms. Detected signals are read, further measurement periods are triggered, and the corresponding signals are read. The measurement periods are repeated for e.g. 1000 times, which gives 1 second for the total measurement time. Finally the measured signals are summed to achieve the result of the total measurement.

In this patent specification the structure of the components in an optical measurement instrument is not described in more detail as they can be implemented using the description above and the general knowledge of a person skilled in the art.

An optical instrument includes control means for performing the optical measurement process. The control of the measuring process in an optical measurement instrument generally takes place in an arrangement of processing capacity in the form of microprocessor(s) and memory in the form of memory circuits. Such arrangements are known as such from the technology of analyzers and relating equipment. To convert a known optical instrument into an equipment according to the invention it may be necessary, in addition to the hardware modifications, to store into the memory means a set of machine-readable instructions that instruct the microprocessor(s) to perform the operations described above. Composing and storing into memory of such instructions involves known technology which, when combined with the teachings of this patent application, is within the capabilities of a person skilled in the art.

Above, an embodiment of the solution according to the invention has been described. The principle according to the invention can naturally be modified within the frame of the scope defined by the claims, for example, by modification of the details of the implementation and ranges of use.

The embodiments described above mainly relate to double emission measurements. However, even if the invention has special advantages when applied to double emission measurements, the invention can as well be applied in other types of measurements, such as single emission measurements.

It is also to be noted that the invention is not in any way restricted to the applications of the photoluminescence measurement. An experienced user is able the use the present invention also in other measurement technologies in common use in biochemical laboratories. For example, e.g. reflectance, turbidimetric and nephelometric measurement can be measured using a fluorescent measurement technology with the exception that the emission filter must be a gray filter.

Although the invention has been described with reference to the different microtitration plates it is equally applicable to any form of sample matrix like gels and filter.

Although the invention is described with the arrangement where the illumination sources and detectors are located on the top measurement head, there is no reason why their location on the bottom measurement head should not work.

What is claimed is:

1. An optical measurement instrument for measuring samples, comprising an illumination source (211) for forming an excitation beam, a detector (231a) for detecting an emission beam, an interface (218, 223, 233a, 233b, 238) for a changeable optical module (240) with a purpose of directing the excitation beam received from the illumination source (211) into the sample (281) and/or directing an emission beam received from the sample (281) to a detector (231a), characterized in that the interface further comprises means (238, 233b) for adapting to at least one of said beams being transmitted through an aperture free from optical surfaces located on a wall of an optical module, and means for focusing said beam in said aperture.

2. An instrument according to claim 1, characterized in that the size of the aperture is arranged to determine the size of the sample area to be measured.

3. An instrument according to claim 1, characterized in that it comprises a first mirror (241) for reflecting the excitation beam received from an illumination source into the sample and for transmitting an emission beam received from the sample.

4. An instrument according to claim 1, characterized in that the instrument comprises a second detector, and the optical module comprises means (242) for dividing the emission beam into a first emission beam for the first detector a second emission beam for the second detector.

5. An instrument according to claim 4, characterized in that said means for dividing the emission beam received from the sample into two emission beams is a second dichroic mirror (242), said mirror transmitting the first emission beam and reflecting the second emission beam.

6. An instrument according to claim 1, characterized in that said interface further comprises means (219) for receiving an illumination reference beam from a further aperture free from optical surfaces of the optical module.

7. An instrument according to claim 6, characterized in that the changeable optical module comprises a third mirror (243), which is a beam splitter mirror for reflecting a part of the light received from the illumination source (211), and the instrument comprises a further detector (219) for measuring the reflected, reference part of the excitation light in order to measure the illuminating effect of the illumination source.

8. An instrument according to claim 7, characterized in that the transmission/reflection properties of said third mirror are application specific.

9. An instrument according to claim 1, characterized in that it comprises a top measurement head (320) for measuring a sample from (320) above the sample (381), wherein the top measurement head comprises a top optical module (340).

10. An instrument according to claim 9, characterized in that the top measurement head (320) comprises means (318T, 340a, 323) for providing an excitation beam to the sample and means (323, 340a, 337a) for measuring a first emission beam from the sample.

11. An instrument according to claim 10, characterized in that the top measurement head comprises means (323, 340a, 338, 337b) for measuring a second emission beam from the sample.

12. An instrument according to claim 1, characterized in that it comprises a bottom measurement head (360) for measuring a sample from below the sample (381), wherein said bottom measurement head (360) comprises a changeable bottom optical module (350) and an optical interface for the bottom optical module.

13. An instrument according to claim 12, characterized in that it comprises an optical fibre (318B) for guiding light between the illumination source and the bottom optical module (350).

14. An instrument according to claim 12, characterized in that it comprises an optical fibre (338a) for guiding the first emission beam between the bottom optical module (350) and the first detector (332a).

15. An instrument according to claim 13, characterized in that the optical interface for the bottom optical module comprises means (338a) for receiving a second emission beam from the optical module (350).

16. An instrument according to claim 13, characterized in that it comprises an optical fibre (338b) for directing the second emission beam between the bottom optical module (350) and the second detector (332b).

17. An instrument according to claim 1, characterized in that said aperture is optically adapted to an end of an optical fibre.

18. A changeable optical module (1340, 1850) for an optical measurement instrument, the module comprising means (1346, 1856) for receiving an excitation beam from an illumination source and means (1341, 1348, 1851, 1858) for directing the excitation beam to a sample, and/or means (1348) for receiving an emission beam from the sample and means (1341, 1344, 1851, 1854) for outputting the emission beam received from the sample to a detector, characterized in that the means for receiving and/or the means for outputting comprise(s) an aperture free from optical surfaces on an outer wall of the optical module module, and means for focusing said beam in said aperture.

19. A changeable optical module according to claim 18, characterized in that the size of the aperture is arranged to determine the size of the sample area to be measured.

20. A changeable optical module according to claim 18, characterized in that it comprises a first mirror (1341) for reflecting the excitation beam received from an illumination source into the sample and for transmitting an emission beam received from the sample.

21. A changeable optical module according to claim 18, characterized in that it comprises a second mirror, which is a dichroic mirror for separating the emission beam received from the sample into two emission beams (1342), said mirror transmitting the first emission beam and reflecting the second emission beam.

22. A changeable optical module according to claim 21, characterized in that said second mirror (1342) is substantially transparent to light of a first wavelength band for transmitting the first emission within said first wavelength band into the first detector, and said second mirror is substantially reflective to light of a second wavelength band for reflecting the second emission within said second wavelength band into the second detector.

23. A changeable optical module according to claim 18, characterized in that the module comprises a third mirror (1343) for reflecting a part of the excitation beam to a detector for measuring the illuminating effect, wherein said third mirror is a beam splitter mirror.

24. A changeable optical module according to claim 23, characterized in that the transmission/reflection properties of said third mirror (1343) are application specific.

25. A changeable optical module according to claim 23, characterized in that it comprises an aperture free from optical surfaces for outputting said reflected part of the excitation beam.

26. A changeable optical module according to claim 18, characterized in that the means for outputting the excitation beam is the same as the means for receiving the emission beam (1348).

27. A changeable optical module according to claim 26, characterized in that said means is an aperture free from optical surfaces.

28. A changeable optical module according to claim 18, characterized in that said means for outputting the emission beam is an aperture free from optical surfaces (1344).

29. A changeable optical module according to claim 18, characterized in that it comprises an aperture free from optical surfaces (1345) for outputting a second emission beam.

30. A changeable optical module according to claim 18, characterized in that said module is adapted for measurement from above a sample to be measured (1340).

31. A changeable optical module according to claim 18, characterized in that said module is adapted for measurement from below a sample to be measured (1850).

32. A changeable optical module according to claim 18, characterized in that said module is adapted to output the first emission beam to an end of an optical fibre (1854).

33. A changeable optical module according to claim 18, characterized in that said module is adapted to output said second emission beam to an end of an optical fibre (1855).

34. A changeable optical module according to claim 18, characterized in that said means for receiving excitation beam is an aperture free from optical surfaces (1346).

35. A changeable optical module according to claim 34, characterized in that said aperture is adapted for receiving the excitation beam from the end of an optical fibre.

36. A changeable optical module according to claim 18, characterized in that at least one aperture free from optical surfaces is located on a wall, said wall or part of it being changeable for changing the size of the aperture.

37. A changeable optical module according to claim 18, characterized in that said module comprises attachment means for manual attachment and detachment of the module to/from the optical measurement instrument.

38. A changeable optical module according to claim 18, characterized in that said module comprises means for attaching to movable base (1228) of an optical measurement instrument, wherein the change of a module used for a measurement is arranged by moving said movable base.

39. A process for measurement of samples with an optical measurement instrument comprising at least one measurement head, possible means for providing excitation of a sample and means for measuring an emission from the sample, the process comprising the phases of selecting a measurement mode (11), selecting at least one changeable optical module for a measurement head, the optical module guiding the excitation beam from an illumination source into the sample (20, 21) and/or guiding at least one emission beam from a sample into at least one detector (20, 21), performing the selected optical measurement (23–25), characterized in that in the step of selecting the optical module, a kind of optical module is selected, which has an aperture free from optical surfaces for receiving an excitation beam and/or for outputting an emission beam, and the beam is focused in said aperture.

40. A method for optical measurement of samples comprising the step of transmitting excitation/emission beam between the sample and a measurement head of an optical instrument, comprising transmitting said beam through an optical module of the measurement head, characterized in that said beam is guided through an aperture free from optical surfaces located on an outer wall of the optical module, and the beam is focused in said aperture.

41. A method according to claim 40, characterized in that it comprises a measurement of two emission beams substantially simultaneously.

42. A method according to claim 41, characterized in that the emission beam received from the sample is divided into two emission beams in the optical module and said two emission beams are guided through separate apertures free from optical surfaces of the optical module.

43. A method according to claim 40, characterized in that a part of the light from the illumination source is reflected, guided through an aperture free from optical surfaces of the optical module, and measured, and illuminating effect of the illumination source is determined on the basis of said measuring.

44. A method according to claim 43, characterized in that the part of the light from the illumination source is reflected with a dichroic mirror within the optical module, wherein the transmission/reflection properties of said third dichroic mirror are application specific.

45. A method according to claim 40, characterized in that the excitation beam is directed to the sample from above the sample, and the emission is measured from above the sample.

46. A method according to claim 40, characterized in that the excitation beam is directed to the sample from below the sample, and the emission is measured from below the sample.

47. A method according to claim 40, characterized in that the method comprises a photoluminescence measurement.

* * * * *